United States Patent [19]

Geiger et al.

[11] 4,420,424

[45] Dec. 13, 1983

[54] NEW PEPTIDES AND A PROCESS FOR THEIR PREPARATION

[75] Inventors: Rolf Geiger, Frankfurt am Main; Wolfgang König, Hofheim am Taunus; Gerd Johnscher, Kelkheim, all of Fed. Rep. of Germany

[73] Assignee: Hoechst Aktiengesellschaft, Frankfurt am Main, Fed. Rep. of Germany

[21] Appl. No.: 319,267

[22] Filed: Nov. 9, 1981

Related U.S. Application Data

[63] Continuation of Ser. No. 188,820, Sep. 19, 1980, abandoned.

[30] Foreign Application Priority Data

Sep. 22, 1979 [DE] Fed. Rep. of Germany ....... 2938420

[51] Int. Cl.$^3$ .......................................... C07C 103/52
[52] U.S. Cl. ............................................. 260/112.5 R
[58] Field of Search ................................ 260/112.5 R

[56] References Cited

U.S. PATENT DOCUMENTS

| 29,595 | 4/1979 | Goldstein et al. | |
| 124,959 | 3/1980 | Goldstein et al. | |
| 4,261,886 | 4/1981 | Goldstein et al. | 260/112.5 R |

FOREIGN PATENT DOCUMENTS

| 18182 | 10/1980 | European Pat. Off. |
| 2408580 | 6/1979 | France . |
| 2408581 | 6/1979 | France . |
| 1565032 | 4/1980 | United Kingdom . |
| 1585736 | 3/1981 | United Kingdom . |

OTHER PUBLICATIONS

Charriere et al., "Binding of Autologous Erythrocytes etc.", Proc. Nat. Acad. Sci. USA 72 (No. 8), 3201–3205 (1975).
Lehninger, "Biochemistry", Worth Publishers, New York, 1970, pp. 43, 67, 755.
Morrison and Boyd, "Organic Chemistry", 2nd Ed., Allyn and Bacon, Boston 1970, p. 1099.

*Primary Examiner*—Delbert R. Phillips
*Attorney, Agent, or Firm*—Curtis, Morris & Safford

[57] ABSTRACT

What are disclosed are pentapeptides, useful for influencing the maturing of T-lymphocytes, of the formula $$, G-K-Q-X-M$$

wherein
G is arginine, lysine, ornithine, or homoarginine, or is an unsubstituted or substituted ω-aminoalkanoyl, ω-guanidinoalkanoyl, or ω-dimethylaminoalkanoyl;
K is a basic amino acid such as lysine, arginine, homoarginine, or ornithine;
Q is L- or D-glutamic acid, d-aspartic acid, or D-α-aminoadipic acid;
X is L-valine or L-isoleucine; and
M is an L- or D-aminoacid having a hydrophobic side chain, or an ester or amide of such an acid.

11 Claims, No Drawings

NEW PEPTIDES AND A PROCESS FOR THEIR PREPARATION

This is a continuation of application Ser. No. 188,820, filed Sept. 19, 1980 now abandoned.

Several peptides have been isolated from thymus extracts and their structure has been elucidated, for example thymosin $\alpha_1$, thymopoietine and the "facteur Thymique serique" (FTS), which inter alia contribute to the differentiation ("maturing") of thymus-dependent lymphocytes (T cells).

In the course of investigations into the dependence of this action [which is, for example, detectable in vitro in its effect on autologous rosette-forming cells from the spleen of mice without thymus analogously to the method of Proc. Natl. Acas. Sci. U.S.A., 72 (1975), page 3201] on the structure of low-molecular weight peptides, it has now been found that suitable peptides which, in accordance with the general properties of their units, can be characterized as follows:

basic-basic-acid-hydrophobic-hydrophobic are all effective in the test mentioned and in other tests.

The invention relates, accordingly, to peptides of the formula

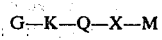

G—K—Q—X—M in which G denotes arginine, lysine, ornithine or homoarginine, in each case in the L- or D-configuration or $\omega$-amino-alkanoyl, $\omega$-guanidino-alkanoyl or $\omega$-dimethylamino-alkanoyl having 3 to 6 C atoms and optionally an $\alpha$-amino group, in the D- or L-configuration, which in turn can carry alkanoyl having 1 to 6 C atoms, aroyl having 7 to 11 C atoms, cycloalkanoyl having up to 2 alkyl C atoms and 5 to 7 cycloalkyl C atoms, aralkanoyl having up to 9 C atoms altogether, wherein a —CH$_2$— group can be replaced by —O— or —S—, alkyloxycarbonyl or aralkyloxycarbonyl having up to 7 C atoms or succinoyl, succinamoyl, glutaroyl, glutaminyl, pyroglutamyl, phthaloyl, phthalamidyl or 2-carboxybenzoyl; K denotes a basic aminoacid, preferably L-lysine, L-arginine, L-homoarginine or L-ornithine; Q denotes L-glutamic acid, D-glutamic acid, D-aspartic acid or D-$\alpha$-aminoadipic acid; X denotes L-valine or L-isoleucine and M denotes an aminoacid having a hydrophobic side chain, in the L- or D-configuration, or an ester, amide, alkylamide or aralkylamide thereof, the alkylamide or alkyl ester having 1 to 6 C atoms or the aralkylamide or aralkyl ester having 7 to 10 C atoms.

The acid function in the characterization shown above is taken care of, in accordance with the invention, by L- and/or D-glutamic acid and by D-aspartic acid and D-$\alpha$-aminoadipic acid; the hydrophobic sector can comprise 1 to 2 aminoacids or amides or esters thereof, Q-I/e or Q-Val as the central sector imparting a particularly advantageous quality of action to the peptides.

The substituent at the $\alpha$-amino group of G and the unit M are not critical for the action, but they affect it quantitatively. Thus, particularly in G, the alkanoyl radical can be a formyl to hexanoyl radical, the aroyl radical can be benzoyl, optionally substituted by methyl, methoxy or chlorine, and the aralkanoyl radical can be phenacetyl, cinnamoyl, dihydrocinnamoyl, phenoxyacetyl or phenylthioacetyl, and the aryl radical can be unsubstituted or substituted by methyl, methoxy or chlorine.

Alkyloxycarbonyl or aralkyloxycarbonyl is preferably ethyloxycarbonyl, isobutyloxycarbonyl, tert.-butyloxycarbonyl, benzyloxycarbonyl, 4-methylbenzyloxycarbonyl, 4-methoxybenzyloxycarbonyl or 4-chlorobenzyloxycarbonyl.

The aminoacid which has a hydrophobic side chain and is represented by M can be, in particular, Ala, Val, Leu, Ile, Met, Phe, Pro, Tyr, or Phg (C-phenylglycine) and can also be an aminoacid having hydrophobic substituents, such as Ser(Bu$^t$), Thr(Bu$^t$), Cys(Bu$^t$), Cys(Et), Cys(Bzl), Glu(OBu$^t$), Asp(OBu$^t$), Glu(NH-Bu$^t$), Glu(NH-Et), Lys(Boc), Orn(Boc), Tyr(Bu$^t$), Tyr(Me), Phe(Cl) or Tyr(Cl), and also tryptophan, substituted by alkyl, halogen or methoxy. Possible alkylamides are preferably n-alkyl alkylamides or branched alkylamides, such as isopropylamide, isobutylamide, tert.-butylamide, 3-methylbutylamide or 3-ethylbutylamide; examples of possible aralkylamides are benzylamide or phenethylamide, which can be substituted by 1 to 2 methyl groups in the nucleus and/or in the side chain. The same alkyl, aryl or aralkyl radicals can also be present in the ester linkage.

The peptides according to the invention have a similarity to a pentapeptide Arg-Lys-Asp-Val-Tyr which has recently been described in Science 204 (1979), page 1309, a part sequence of thymopoietin, which is regarded as the sector of this peptide which is supposed to be responsible for its biological action. It is interesting that this sequence corresponds to the succession basic-basic-acid-hydrophobic-hydrophobic mentioned above, which thus appears to be an overriding principle for peptides having the thymus activity mentioned.

In contrast with this peptide, however, the peptides according to the invention contain L- or D-glutamic acid and also D-aspartic acid or D-$\alpha$-aminoadipic acid as the acid aminoacid. Peptides of glutamic acid and $\alpha$-aminoadipic acid are considerably more stable than aspartic acid peptides in a weakly acid medium, in which these compounds are mostly used. Aspartic acid peptides undergo a rearrangement via aspartimide peptides, mainly into isoasparagine peptides, so that, for example, it is not possible to heat-sterilize aspartic acid peptides. However, the rearrangement still takes place at a noticeable rate at room temperature and even at refrigerator temperature. If Q is represented by the acid D-aminoacids, the stability of the peptides towards enzymes is increased.

In addition, the compounds according to the invention also include tripeptide and tetrapeptide derivatives, the action of which is in many cases the same as, or even greater than a pentapeptide, prepared in accordance with the invention, having the sequence Lys-Lys-Glu-Val-Val.

The invention also relates to a process for the preparation of the said peptides, which comprises synthesizing, in accordance with methods of peptide syntheses, aminoacid sequences of the formula

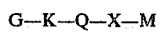

G—K—Q—X—M in which G, K, Q, X and M have their earlier meaning.

The synthesis of the compounds according to the invention follows the known methods of peptide chemistry, such as are described in detail, for example in Houben-Weyl, Methoden der Organischen Chemie (Methods of Organic Chemistry), Volume 15. The examples shown on the following pages illustrate the synthetic processes, which are in themselves known.

The abbreviations customary in peptide chemistry are used, in particular the following:
Boc tert.-butoxycarbonyl
Z benzyloxycarbonyl
Adoc adamantyloxycarbonyl
Me methyl
Bzl benzyl
Bu$^t$ tert.-butyl
Ipr isopropyl
Tcp 2,4,5-trichlorophenyl
HONSu N-hydroxysuccinimide
HOBt 1-hydroxybenzotriazole
DCC dicyclohexylcarbodiimide
Glu pyroglutamyl TLC also stands for thin layer chromatography and HPLC stands for high performance liquid chromatography. In the aminoacid analyses, Glu is taken as 100.

In vitro and in the presence of liver homogenates, the peptides according to the invention have a considerably prolonged life, compared with natural thymus peptides. The compounds in which Q is represented by an acid D-aminoacid, such as D-glutamic acid or D-α-aminoadipic acid, should be singled out particularly. Their action can be demonstrated, for example, in vitro by their effect on T-lymphocytes which form SRBC rosettes, from the blood of patients deficient in immunity or human umbilical cord blood analogously to the methods of J. Exptl- Med. 136 (1972) page 207; Anm. N.Y. Acad. Sci. 249 (1975) page 308 and Int. Archs. Allergy appl. Immun. 53 (1977) page 242, and also their effect on the PHA-induced lymphoblast transformation of human and animal lymphocytes analogously to the methods of J. Exptl. Med. 131 (1970), page 1049, and Cell. Immunol. 16 (1975), page 413. (SRBC=sheep red blood cell; PHA=phytohaemagglutinin).

The compounds according to the invention can be used for treating deficiencies of immunity, viral and fungoid, and also chronic bacterial infections and autoimmunity diseases, and also for the therapy of illnesses caused by cells having immunologically relevant changes in the cell membrane characteristics (for example tumor cells).

In this sense, the invention also relates to the use of the said peptides very generally for influencing the maturing of T-lymphocytes.

EXAMPLE 1

Arg-Arg-Glu-Val-Val-NH-Bzl acetate 28.8 g of Adoc-Arg(Adoc)$_2$-Arg(Adoc)$_2$-Glu(OBu$^t$)-OH.2H$_2$O, prepared as in Chem. Ber. 103 (1970), page 1727, and 6.8 g of H-Val-Val-NH-Bzl.HCl, prepared using L-valine as the aminoacid analogously to Ann. Chem. 655 (1962), page 211, are dissolved in 120 ml of dimethylformamide. 2.7 g of HOBt and 2.6 ml of N-ethylmorpholine are added and 5.0 g of DCC are introduced at room temperature, while stirring. After 15 hours the mixture is filtered and the solvent is distilled off in vacuo. The residue is triturated successively with water, 1 N citric acid, saturated sodium bicarbonate solution and water and is dried. The protective groups are split off by dissolving the residue in 25 ml of trifluoroacetic acid and precipitating the crude pentapeptide derivative with ether after 40 minutes. The resulting trifluoroacetate is first converted, by stirring with a strongly basic ion exchanger in the acetate form in 50 percent strength methanol, into the acetate, which is in the form of a resinous, semi-solid mass after the exchanger has been filtered off and the solvent has been removed by distillation. This is purified by dissolving it in 40 ml of 1 percent strength acetic acid and chromatographing the solution over Sephadex ® LH-20 in a 4×200 cm column. The fractions containing peptide are checked by thin layer chromatography and are collected and lyophilized. The yield of peptide-benzylamide acetate which is a single substance according to TLC is 10.4 g. Aminoacid analysis: Glu 1.00, Val 1.87 and Arg 1.99. No valine was found in the Dansyl determination of end groups.

EXAMPLE 2

Arg-Arg-Glu-Val-Phe-OMe acetate 28.8 g of Adoc-Arg(Adoc)$_2$-Arg(Adoc)$_2$-Glu(OBu$^t$)-OH.2.5H$_2$O are reacted analogously to Example 1 with 6.3 g of H-Val-Phe-OMe.HCl, prepared as in J.Amer.-Chem. Soc. 84 (1962), page 2417, and 9.4 g of peptide are obtained after splitting off the protective groups and purifying the product. Aminoacid analysis: Glu 1.00, Val 0.97, Phe 1.01 and Arg 2.04.

EXAMPLE 3

Arg-Arg-Glu-Val-Tyr-NH$_2$ acetate

The procedure followed is as in Example 1, but 5.6 g of H-Val-Tyr-NH$_2$, prepared as in Chem. Ber. 97 (1964), page 1197, are employed and 9.0 g of the title compound are obtained in the form of the acetate after splitting off the protective groups and purifying the product. Aminoacid analysis: Glu 1.00, Val 0.96, Tyr 0.88 and Arg 2.02.

EXAMPLE 4

Arg-Arg-Glu-Ile-Cys(Bzl)-OEt acetate

The benzyloxycarbonyl group is split off from Z-Ile-Cys(Bzl)-OEt, prepared as in J.Amer.Chem.Soc. 83 (1961), page 145, by treatment with HBr/glacial acetic acid for 30 minutes, and the hydrobromide H-Ile-Cys(Bzl)-OEt.HBr is obtained as a crystalline, somewhat hygroscopic mass after precipitation with ether and reprecipitation from EtOH/ether twice and drying in a desiccator over KOH. 7.0 g of this compound are reacted analogously to Example 1 with 2.88 g of the carboxyl component and 11.2 g of the title compound are obtained in the form of the acetate after splitting off the protective groups and purifying the product. Aminoacid analysis: Glu 1.00, Ile 0.91, Cys(Bzl) 0.92 and Arg 2.01.

EXAMPLE 5

Arg-Arg-Glu-Val-Val-O-CH(CH$_3$)$_2$ acetate (A) Boc-Val-Val-OIpr 5.38 g of H-Val-OIpr.HCl, prepared in a known manner by esterifying L-valine with HCl/isopropanol, are dissolved in 20 ml of dimethylacetamide and 4.0 ml of N-ethylmorpholine are added. At the same time, symmetrical Boc-Val anhydride is prepared from 13.1 g of Boc-Val-OH and 6.6 g of DCC in 50 ml of dimethylacetamide at 0°. The two solutions are combined and allowed to come to room temperature and the mixture is stirred for a further 4 hours at about 22° C. and the solvent is removed by distillation in vacuo. The residue is taken up in 150 ml of ethyl acetate and is extracted by shaking with three times 20 ml of water. After drying over sodium sulfate, the ethyl acetate is removed by distillation and the residue is recrystallized from hexane.

Yield 6.9 g, melting point 126°–129° C.; elementary analysis (C, H and N) correct.

(B) H-Val-Val-OIpr, CF₃COOH

The Boc compound is dissolved in 60 ml of trifluoroacetic acid. After 40 minutes 1:1 ether/petroleum ether is used to produce a precipitate, which is digested thoroughly with the same mixture. After drying in vacuo over KOH the yield is 6.1 g, melting point 172°–174° C. Elementary analysis (N and F) correct.

(C) Arg-Arg-Glu-Val-Val-OIpr acetate 3.7 g of the compound obtained in accordance with (B) are reacted analogously to Example 1 with 14.4 g of Adoc-Arg(Adoc)₂-Arg(Adoc)₂-Glu(OBu$^t$)-OH.2H₂O, 1.35 g of HOBt, 1.3 ml of N-ethylmorpholine and 2.5 g of DCC and 5.8 g of peptide are obtained after splitting off the protective groups and purifying the product. Aminoacid analysis: Glu 1.00, Val 1.90 and Arg 2.07.

EXAMPLE 6

Arg-Arg-Glu-Val-Lys(Z)-OMe acetate

(A) Boc-Val-Lys(Z)-OMe 4.35 g of Boc-Val-OH and 6.6 g of H-Lys(Z)-OMe.HCl are subjected to a condensation reaction with 4.4 g of DCC in 50 ml of CH₂Cl₂, with the addition of 2.7 g of HOBt and 2.6 ml of N-ethylmorpholine (NEM). After filtering the mixture, the solvent is removed by distillation. The residue is taken up in ethyl acetate, washed successively with 2 N acetic acid, 1 M sodium bicarbonate and water and dried over sodium sulfate and, after removing the ethyl acetate by distillation, is recrystallized from diisopropyl ether. Yield 3.5 g, melting point 100°–102°, elementary analysis (C, H and N) correct.

(B) H-Val-Lys(Z)-OMe CF₃COOH

The Boc radical is split off analogously to Example 5 (B). Yield 3.1 g. Almost a single substance in the TLC.

(C) Arg-Arg-Glu-Val-Lys(Z)-OMe acetate 2.5 g of the compound obtained in accordance with (B) are reacted analogously to Example 1 with 7.2 g of carboxyl component, 0.65 ml of NEM, 0.7 g of HOBt and 1.1 g of DCC. After splitting off the protective groups and purifying the product analogously to Example 1, 3.2 g of the title compound are obtained in the form of the acetate. Aminoacid analysis: Glu 1.00, Val 0.97, Lys 1.02 and Arg 1.99.

EXAMPLE 7

Arg-Arg-Glu-Ile-OIpr acetate

Isoleucine isopropyl ester-hydrochloride is prepared in a known manner from isoleucine and HCl/isopropanol. 2.1 g of this compound are reacted analogously to Example 5 (C) with 14.4 g of Adoc-Arg(Adoc)₂-Arg(Adoc)₂-Glu(OBu$^t$)-OH.2H₂O and the product is worked up. Yield 6.2 g. Aminoacid analysis: Glu 1.00, Ile 0.95 and Arg 2.06.

EXAMPLE 8

Glu-Arg-Arg-Glu-Ile-OIpr acetate 8.5 g of the compound obtained in accordance with Example 7 are reacted in 50 ml of dimethylformamide with 3.5 g of L-pyroglutamic acid trichlorophenyl ester in the presence of 0.2 g of HOBt. After 4 hours ethyl acetate is used to precipitate a crude product, which is purified by HPLC on SiO₂ using the system 3:2:1 chloroform/methanol/acetic acid. Yield 5.3 g. Aminoacid analysis: Glu 2.00, Ile 0.92 and Arg 1.98.

EXAMPLE 9

Z-Arg-Arg-Glu-Val-Val-NH₂ acetate

(A) H-Val-Val-NH₂.HCl 7.53 g of Z-Val-OH, 5.91 g of H-Val-NH₂.HBr and 4.05 g of HOBt are dissolved in 40 ml of dimethylformamide. 3.9 ml of N-ethylmorpholine are added to the mixture, followed by 6.6 g of DCC at 0° C. The mixture is stirred for 1 hour at 0° and for 3 hours at room temperature. A thick white mash is formed, which is stirred with 150 ml of water and 50 ml of saturated NaHCO₃ solution. The precipitate is filtered off and dried over P₂O₅ in vacuo. Yield 16.6 g. The substance is a mixture of Z-Val-Val-NH₂ and dicyclohexylurea. 14.85 g of the substance thus obtained are suspended in 40 ml of glacial acetic acid. After adding 40 ml of 4 N HBr/glacial acetic acid, the substance dissolves. The mixture is allowed to stand for one hour at room temperature and a smeary precipitate is produced by means of 400 ml of ether. The liquid is decanted off and the residue is dissolved in 60 ml of methanol. A white, crystalline substance is precipitated by means of 200 ml of ether. After drying over P₂O₅ the yield is 6.7 g, melting point 274°–278° C., $[\alpha]_D^{23} = +5.9°$ (c=1, in methanol).

(B) Z-Glu(OBu$^t$)-Val-Val-NH₂

10.4 g of Z-Glu(OBu$^t$)-OTcp are added to a solution of 6 g of H-Val-Hal-NH₂.HBr, 2.7 g of HOBt and 2.6 ml of N-ethylmorpholine in 20 ml of dimethylformamide. The mixture immediately becomes gelatinous. It is diluted with 75 ml of dimethylformamide and stirred for a further 2 hours. The mixture is then stirred into 900 ml of water containing 50 ml of saturated NaHCO₃ solution. The precipitate is filtered off, triturated with about 200 ml of ethyl acetate and is filtered off again and rinsed with ethyl acetate. Yield 6.55 g, melting point 256°–257°. $[\alpha]_D^{23} = +4.7°$ (c=1, in dimethylacetamide).

(C) H-Glu(OBu$^t$)-Val-Val-NH₂.HCl 6 g of Z-Glu(OBu$^t$)-Val-Val-NH₂ are suspended in 200 ml of methanol. After adding Pd-on-BaSO₄ and 2 N methanolic hydrochloric acid, the mixture is subjected to catalytic hydrogenation at pH 4.5. When the reaction is complete, the catalyst is filtered off and the filtrate is concentrated. The residue crystallizes on being triturated with ether. Yield 4.8 g, melting point 211°–219°, $[\alpha]_D^{23} = -18.7°$ (c=1, in methanol).

(D) Z-Arg-Arg-Glu-Val-Val-NH₂ acetate 6.3 g of Z-Arg-Arg-OH.2 HBr, prepared as in Experientia (Basel) 12, (1956), page 446, and 4.4 g of the compound obtained under (C) are dissolved in 50 ml of dimethylformamide. 1.35 g of HOBt, 1.3 ml of N-ethylmorpholine and 2.2 g of DCC are added successively, while stirring, and stirring is continued for a further 5 hours. The mixture is then filtered and the filtrate is concentrated in vacuo. The tert.-butyl ester group is split off with trifluoroacetic acid and the product is converted into the acetate and purified analogously to Example 1. Yield 4.5 g. Aminoacid analysis: Glu 1.00, Val 1.88 and Arg 2.02.

EXAMPLE 10

D-Arg-Lys-Glu-Val-Val-OMe acetate

(A) H-Val-Val-OMe.HCl 30 g of Z-Val-Val-OMe (prepared as in Chem. Ber. 103, 788–798 (1970)) are dissolved in 250 ml of methanol and subjected to catalytic hydrogenation at pH 4 after adding methanolic hydrochloric acid and Pd-on-BaSO$_4$. When the reaction is complete, the catalyst is filtered off and the filtrate is concentrated. The resulting oil is triturated with ether. The substance crystallizes after a little time. It is filtered off and rinsed with ether. The substance is hygroscopic and is dried over P$_2$O$_5$ in vacuo. Yield 18.8 g, melting point 153°. $[\alpha]_D^{23} = +2.5°$ (c=1, in methanol).

(B) Z-Glu(OBu$^t$)-Val-Val-OMe 6.5 ml of N-ethylmorpholine are added to a solution of 13.3 g of H-Val-Val-OMe.HCl and 7.75 g of HOBt in 50 ml of dimethylformamide, and 25.85 g of Z-Glu(OBu$^t$)-OTcp are added while stirring. After three hours the mixture is stirred with 300 ml of water and 100 ml of saturated NaHCO$_3$ solution. The precipitate produced is filtered off and dissolved in 100 ml of ethyl acetate. The ethyl acetate phase is extracted by shaking, once in each case, with 50 ml of K$_2$SO$_4$/KHSO$_4$ solution, 50 ml of saturated NaHCO$_3$ solution and water and is dried over Na$_2$SO$_4$ and concentrated. The residue is triturated with petroleum ether and filtered off. Yield 23.6 g, melting point 138°–142°. The product is purified further by recrystallization from 100 ml of ethyl acetate. Yield 13.25 g, melting point 173°, $[\alpha]_D^{23} = =42.4°$ (c=1, in methanol).

(C) H-Glu(OBu$^t$)-Val-Val-OMe.HCl 13 g of Z-Glu(OBu$^t$)-Val-Val-OMe are suspended in about 150 ml of methanol. The suspension is subjected to catalytic hydrogenation at pH 4.5 after adding Pd-on-BaSO$_4$ and 2 N methanolic hydrochloric acid. When the reaction is complete the catalyst is filtered off and the filtrate is concentrated. The residue crystallizes on being triturated with ether. Yield 9.55 g, melting point 192°, $[\alpha]_D^{23} = -20.9°$ (c=1, in methanol).

(D) Z-Lys(Boc)-Glu(OBu$^t$)-Val-Val-OMe

A solution of 5.6 g of Z-Lys(Boc)-OTcp in 15 ml of dimethylformamide is added to a solution of 4.52 g of H-Glu(OBu$^t$)-Val-Val-OMe.HCl, 1.35 g of HOBt and 1.3 ml N-ethylmorpholine in 10 ml of dimethylformamide. The solution is stirred for two hours at room temperature and 200 ml of water and 25 ml of saturated NaHCO$_3$ solution are added. The precipitate is filtered off and dissolved in 100 ml of ethyl acetate. Water is separated off in a separating funnel. The ethyl acetate phase is dried with Na$_2$SO$_4$ and concentrated to about 50 ml. 200 ml of petroleum ether are added to it, the mixture is cooled to 0° C. and the product is filtered off. Yield 7.6 g, melting point 171°–177°, $[\alpha]_D^{23} = -36.6°$ (c=1, in methanol).

(E) H-Lys(Boc)-Glu(OBu$^t$)-Val-Val-OMe.HCl 7 g of Z-Lys(Boc)-Glu(OBu$^t$)-Val-Val-OMe are dissolved in 150 ml of methanol. The solution is subjected to catalytic hydrogenation at pH 4.5 after adding Pd-on-BaSO$_4$ and 2 N methanolic hydrochloric acid. When the reaction is complete, the catalyst is filtered off and the filtrate is concentrated. The residue crystallizes on being triturated with ether. Yield 5.45 g, melting point 194°–198°, $[\alpha]_D^{23} = -33.1°$ (c=1, in methanol).

(F) D-Arg-Lys-Glu-Val-Val-OMe acetate 1.37 g of Boc-D-Arg-OH and 3.4 g of the compound obtained in accordance with (E) are dissolved in 30 ml of dimethylformamide. 0.68 g of HOBt and 1.05 g of DCC are added and the mixture is stirred overnight. It is then filtered and the filtrate is concentrated in vacuo. The residue is taken up in 20 ml of trifluoroacetic acid in order to split off the protective groups. After 30 minutes the crude peptide is precipitated by means of ether and converted analogously to Example 1 into the acetate, which is purified by chromatography on Sephadex ® LH-20. Yield 3.0 g. Aminoacid analysis: Glu 1.00, Val 1.92, Lys 0.98 and Arg 1.01.

EXAMPLE 11

Z-Arg-Arg-Glu-Val-Val-OMe acetate

(A) Z$_3$-Arg-Glu(OBu$^t$)-Val-Val-OMe 1.3 ml of N-ethylmorpholine and 7.6 g of Z$_3$-Arg-OTcp, dissolved in 15 ml of dimethylformamide, are added to a solution of 4.52 g of H-Glu(OBu$^t$)-Val-Val-OMe.HCl and 1.35 g of HOBt in 10 ml of dimethylformamide. After 2 hours the reaction mixture is stirred with 200 ml of water and 25 ml of saturated NaHCO$_3$ solution. The precipitate is filtered off and washed with water. The substance is dissolved, while still wet, in 400 ml of ethyl acetate on a steam bath. The ethyl acetate solution is dried with Na$_2$SO$_4$ and concentrated to about 100 ml. 200 ml of petroleum ether are added to the residue, the mixture is briefly cooled and the product is filtered off and washed with petroleum ether. Yield 8.6 g, melting point 204°–209°, $[\alpha]_D^{23} = -2.4°$ (c=1, in dimethylacetamide).

(B) H-Arg-Glu(OBu$^t$)-Val-Val-OMe.2HCl 8 g of Z$_3$-Arg-Glu(OBu$^t$)-Val-Val-OMe are suspended in 150 ml of methanol and 40 ml of dimethylformamide and the suspension is subjected to catalytic hydrogenation at pH 4.5 after adding Pd-on-BaSO$_4$ and 2 N methanolic hydrochloric acid. When the reaction is complete the catalyst is filtered off and the filtrate is concentrated. The residue is triturated with ether. The ether is decanted off and the oil is dried in a high vacuum. Yield 5.1 g of an amorphous foam.

(C) Z-Arg-Arg-Glu-Val-Val-OMe acetate 0.68 g of HOBt and 1.1 g of DCC are added successively to 1.54 g of Z-Arg-OH and 3.44 g of the compound prepared in accordance with (B), in 40 ml of dimethylformamide. After stirring overnight, the mixture is filtered, the filtrate is concentrated in vacuo and the residue is digested with ethyl acetate. The tert.-butyl group is split off analogously to Example 1 with trifluoroacetic acid and the compound is converted into its acetate and purified by chromatography on Sephadex ® LH 20. Yield 2.9 g, aminoacid analysis: Glu 1.00, Val 1.89 and Arg 2.01.

EXAMPLE 12

Z-Lys-Arg-Glu-Val-Val-OMe acetate 6.4 g of H-Arg-Glu(OBu$^t$)-Val-Val-OMe.2HCl, prepared in accordance with Example 11 (B), are dissolved in 80 ml of dimethylacetamide together with 4.0 g of Z-Lys(Boc)-ONSu, 1.28 ml of N-ethylmorpholine and 1.35 g of HOBt. 2.2 g of DCC are added to the mixture, which is stirred overnight and filtered and the filtrate is concentrated in vacuo. The residue is digested with ethyl acetate. The tert.-butyl protective groups are split off and the product is converted into its acetate and purified on Sephadex ® LH 20 analogously to Example 1. Yield 5.8 g. Aminoacid analysis: Glu 1.00, Val 1.90, Lys 1.03 and Arg 1.00.

EXAMPLE 13

D-Lys-Arg-Glu-Val-Val-OMe acetate

The procedure of Example 12 is followed, but Z-D-Lys(Boc)-ONSu is employed. The crude product is subjected to catalytic hydrogenation over Pd in 90 percent strength acetic acid. A procedure analogous to Examples 12 and/or 1 is then followed in order to split off Boc and Bu$^t$, to convert the product into its acetate and to purify the latter subsequently. Yield 6.0 g. Aminoacid analysis: Glu 1.00, Val 1.89, Lys 0.99 and Arg 1.02.

EXAMPLE 14

Ethoxycarbonyl-Lys-Lys-Glu-Val-Val-OMe acetate 6.8 g of H-Lys(Boc)-Glu(OBu$^t$)-Val-Val-OMe.HCl, prepared in accordance with Example 10 (E), 4.0 of Z-Lys(Boc)-ONSu and 1.28 ml of N-ethylmorpholine in 70 ml of dimethylformamide are stirred overnight. The solvent is removed by distillation in vacuo and the residue is taken up in moist 10:1 ethyl acetate/n-butanol. After washing with a saturated NaHCO$_3$-solution and water, the solution is dried over sodium sulfate and the solvent is removed by distillation in vacuo. The resinous residue is dissolved in 100 ml of methanol and subjected to catalytic hydrogenation over Pd at pH 4, reached by titration with 2 N HCl in methanol. After filtering off the catalyst, the filtrate is evaporated to dryness, the solid residue is taken up in 50 ml of dimethylformamide and 4.0 g of ethyl pentachlorophenyl carbonate are added [Bull. Soc. Chim. France 23 (1900), page 818]. The mixture is stirred overnight, the solvent is removed by distillation in vacuo and the residue is digested with ether. A procedure analogous to that of Example 1 is followed in order to split off the protective groups, to convert the product into its acetate and to purify the latter. Yield 4.1 g. Aminoacid analysis: Glu 1.00, Val 1.92 and Lys 2.02.

EXAMPLE 15

2-Carboxybenzoyl-Arg-Arg-Glu-Val-Val-OIpr acetate 8.2 g of H-Arg-Arg-Glu-Val-Val-OIpr acetate (Example 5 C) and 1.5 g of phthalic anhydride are dissolved in 50 ml of 2:1 N-methylpyrrolidone/pyridine. 1.35 g of HOBt are added and the mixture is stirred for 4 hours. Ether is then used to precipitate a crude product which, after being re-precipitated from methanol/ethyl acetate, is nearly a single substance according to thin layer chromatography. The by-products are less than 5%. Yield 6.9 g. Aminoacid analysis as in starting material. No free α-amino group can be detected by the Dansyl method.

EXAMPLE 16

Succinoyl-Arg-Arg-Glu-Val-Val-OIpr acetate

The procedure of Example 15 is followed, but 1.1 g of succinic anhydride are employed instead of the phthalic anhydride and the product is worked up as described under Example 15. Yield 6.1 g. No free α-amino group can be detected by the Dansyl method.

EXAMPLE 17

Cyclohexylacetyl-Arg-Arg-Glu-Val-Val-NH-Bzl acetate

A solution of 1.5 g of cyclohexylacetyl chloride in 5 ml of methylene chloride is added dropwise, at 0°–4° C. and while stirring, to a solution of 7.1 g of H-Arg-Arg-Glu-Val-Val-NH-Bzl acetate, prepared as in Example 1, in 40 ml of dimethylacetamide, the mixture is allowed to react for a further 1 hour and the crude reaction product is precipitated with ether. The Boc group is precipitated analogously to the Adoc group in Example 1. The product is converted into the form of its acetate, again analogously to Example 1, and the latter is purified by chromatography on Sephadex ® LH 20. Yield 4.8 g. Aminoacid analysis: Glu 1.00, Val 1.88 and Arg 1.97.

EXAMPLE 18

ε-Aminocaproyl-Arg-Glu-Val-Val-OMe acetate

The activated ester is prepared from 2.31 g of Boc-ε-aminocaproic acid, 1.15 g of HONSu and 2.02 g of DCC in 10 ml of dimethylformamide, the precipitated dicyclohexylurea is filtered off, the filtrate is combined with a solution of 5.2 g of Arg-Glu(OBu$^t$)-Val-Val-OMe.2HCl (Example 11 B) in 25 ml of dimethylformamide and 1.03 ml of N-ethylmorpholine are added. After standing overnight, the solvent is removed by distillation in vacuo and the residue is digested with ethyl acetate. The protective group is split off and the product is purified analogously to Example 1. Yield 3.6 g, aminoacid analysis: Glu 1.00, Val 1.90, ε-Cap 1.03 and Arg 1.01.

EXAMPLE 19

ε-Guanidocaproyl-Arg-Glu-Val-Val-OMe acetate 2 g of the compound obtained in accordance with Example 18 are dissolved in 10 ml of water. A solution of 11 g of O-methylisourea hydrochloride in 30 ml of water is added and the pH of the solution is kept at 9 by means of 2 N NaOH. After 20 hours a part of the water is distilled off in vacuo. The resulting concentrated solution is demineralized over a column of Biogel ® P2 (4×200 cm), the peptide being purified at the same time. Yield 1.2 g. The peptide is purified further by being adsorbed onto the strongly acid ion exchanger Lewatit S 100 in a 2×50 cm column and is eluted fractionally using 0.2 N ammonia. The change of concentration in the eluate caused by the peptides issuing from the column is determined by means of the refractive index (differential refractometer). Yield, after lyophilizing the fraction, redissolving in 5 percent strength acetic acid and lyophilizing again, 0.6 g. Aminoacid analysis: Glu 1.00, Val 1.88, ε-guanidocaproyl not determined, ε-aminocaproyl <0.02 and Arg 1.01.

EXAMPLE 20

N$^ε$-Dimethyl-D-lysyl-Lys-Glu-Val-Val-OMe acetate 6.8 g of H-Lys(Boc)-Glu(OBu$^t$)-Val-Val-OMe.HCl, obtained in accordance with Example 10, are reacted analogously to Example 10 and 12 with 4.0 g of Boc-B-Lys(Z)-ONSu and 7 g of crude Boc-D-Lys(CH$_3$)$_2$-Lys(-Boc)-Glu(OBu$^t$)-Val-Val-OMe are obtained after catalytic hydrogenation in 50 ml of methanol in the presence of 5 ml of 30 percent strength formaldehyde. The protective groups are split off with trifluoroacetic acid, the product is converted into its acetate and is purified all analogously to Example 1. Yield 2.9 g. Aminoacid analysis: Glu 1.00, Val 1.90, Lys 1.01 and N-ε-dimethyllysine 0.93.

EXAMPLE 21

Lys-Arg-Glu-Val-Thr(Bu$^t$)-OBu$^t$ acetate (A) H-Val-Thr(Bu$^t$)-OBu$^t$.HCl 25.1 g of Z-Val-OH and 23.1 g of H-Thr(Bu$^t$)-OBu$^t$ are reacted in 200 ml of tetrahydrofuran in the presence of 13.5 g of HOBt with 22 g of DCC, the mixture is filtered after stirring overnight, the solvent is removed by distillation, the residue is taken up in 300 ml of ethyl acetate, the solution is washed successively with 2 N citric acid (0° C.), saturated sodium bicarbonate and water and is dried over sodium sulfate and, after filtration, the ethyl acetate is removed by distillation. The residue is dissolved in 400 ml of methanol. The solution is subjected to catalytic hydrogenation over Pd at pH 4, while titrating with 2 N methanolic HCl, the catalyst is filtered off when the reaction is complete and the solution is evaporated to dryness. The solid residue is digested with ether and dried in vacuo. Melting point 135°–140° (decomposition). Elementary analysis (C, H, N and Cl) correct. Yield 28.3 g.

(B) Z-Glu(OBzl)-Val-Thr(Bu$^t$)-OBu$^t$ 25.7 g of H-Val-Thr(Bu$^t$)-OBu$^t$.HCl are reacted, in 250 ml of dimethylformamide, with 26.0 g of Z-Glu-(OBzl)-OH and 15 g of DCC in the presence of 9.5 g of HOBt. After stirring for 6 hours the mixture is filtered and the filtrate is evaporated to dryness in vacuo. The residue is taken up in ethyl acetate, the solution is washed as described under (A) and, after drying and evaporating off the solvent, 37.3 g of the title compound are obtained with a melting point of 140°–144° (decomposition). Elementary analysis correct (C, H and N).

(C) Glu-Val-Thr(Bu$^t$)-OBu$^t$

The compound obtained in accordance with (B) is subjected to catalytic hydrogenation over Pd in 80 percent strength methanol. The catalyst is filtered off and the solution is evaporated to dryness in vacuo. Triturating the residue with ether leads to a compound which is pure according to chromatography.

(D) Lys-Lys-Glu-Val-Thr(Bu$^t$)-OBu$^t$ acetate 6.8 g of Z-Lys(Z)-Lys(Z)-OH, obtained as in Chem. Ber. 93 (1960), page 2387, are preactivated with 1.35 g of HOBt and 2.06 g of DCC in 30 ml of dimethylacetamide. The solution is filtered and the filtrate is combined with a solution in 30 ml of N-methylpyrrolidone of 4.6 g of the compound obtained in accordance with (C). After 15 hours the solvent is removed by distillation in vacuo, the residue is taken up in 90 percent strength acetic acid and the solution is subjected to catalytic hydrogenation over Pd. After filtering off the catalyst, removing the solvent by distillation, digesting the residue with ether and drying, a crude product is obtained which is purified by chromatography on silica gel using the system 3:3:1:1 chloroform:methanol:acetic acid:water. Yield 6.1 g. Aminoacid analysis: Glu 1.00, Thr 0.89, Val 0.92 and Lys 2.05.

EXAMPLE 22

Lys-Lys-Glu-Val-Val-OBu$^t$ acetate (A) H-Val-Val-OBu$^t$.HCl 37.7 g of Z-Val-OH, 31.4 g of H-Val-OBu$^t$.HCl and 19.75 g of HOBt are dissolved in 200 ml of dimethylformamide. 19.5 ml of N-ethylmorpholine are added to the solution, followed by 33 g of DCC at 0° C. The mixture is stirred for 1 hour at 0° C. and for 1 hour at room temperature, the precipitate is filtered off and the filtrate is concentrated in vacuo. The residue is partitioned between 200 ml of ethyl acetate and 200 ml of water. The ethyl acetate phase is then extracted by shaking with 150 ml of saturated NaHCO$_3$ solution, 150 ml of K$_2$SO$_2$/KHSO$_4$ solution, 150 ml of saturated NaHCO$_3$ solution and 150 ml of water and is dried over Na$_2$SO$_4$ and concentrated. The resulting oil (60 g) is dissolved in 300 ml of methanol and subjected to catalytic hydrogenation at pH 4.5 after adding methanolic hydrochloric acid and Pd-on-BaSO$_4$. When the reaction is complete the catalyst is filtered off and filtrate is concentrated. The residue crystallizes from ether. Yield 40 g. Melting point 191°–194°, $[\alpha]_D^{23} = -8.3°$ (c=1, in methanol).

(B) H-Glu-Val-Val-OBu$^t$ 31 g of H-Val-Val-OBu$^t$.HCl are subjected, analogously to Example 21 (B), to a condensation reaction with 37 g of Z-Glu(OBzl)-OH in dimethylformamide in the presence of 13.5 g of HOBt and 12.8 ml of N-ethylmorpholine, by means of 22 g of DCC. After working up analogously to this example, catalytic hydrogenation is carried out as described in Example 21 (C). The compound insoluble in ether is isolated and is a single substance according to thin layer chromatography. Yield 51 g.

(C) Lys-Lys-Glu-Val-Val-OBu$^t$ acetate 6.8 g of Z-Lys(Z)-Lys(Z)-OH are preactivated analogously to Example 21 (D), the resulting solution is reacted with a solution, in 30 ml of dimethylformamide, of 4.2 g of the compound obtained in accordance with (B) and the product is worked up as described in Example 21 (D). Yield 5.85 g. Aminoacid analysis: Glu 1.00, Val 1.87 and Lys 1.99.

EXAMPLE 23

Lys-Lys-Glu-Ile-Val-OBu$^t$ acetate (A) Z-Ile-Val-OBu$^t$ 163.7 g of Z-Ile-OH dicyclohexylammonium salt are partitioned between 600 ml of ethyl acetate and 370 ml of 1 N sulfuric acid, while stirring. The ethyl acetate phase is extracted with water, dried over Na$_2$SO$_4$ and concentrated. The residue is dissolved, together with 73.15 g of H-Val-OBu$^t$.HCl and 47.25 g of HOBt, in 350 ml of dimethylformamide. 44.8 ml of N-ethylmorpholine are added to the mixture, followed, at 0° C., by a solution of 73.5 g of DCC in 100 ml of dimethylformamide. The mixture is stirred for 1 hour at 0° C. and overnight at room temperature. On the following day the precipitate is filtered off and the filtrate is concentrated in a high vacuum. The resulting oil is dissolved in 500 ml of ethyl acetate and the solution is extracted by shaking successively with 400 ml of water, 400 ml of K$_2$SO$_4$/KHSO$_4$ solution, 400 ml of saturated NaHCO$_3$ solution and 400 ml of water. The ethyl acetate phase is dried over Na$_2$SO$_4$ and concentrated. The substance is dissolved in 1,000 ml of petroleum ether and the solution is filtered and cooled to 4° C. overnight. On the following day the compound which has precipitated out is filtered off. Yield 110.5 g, melting point 104°–105°, $[\alpha]_D^{23} = -39.9°$ (c=1, in methanol).

(B) H-Ile-Val-OBu$^t$.HCl 105 g of Z-Ile-Val-OBu$^t$ are dissolved in 1,000 ml of methanol and subjected to catalytic hydrogenation at pH 4.5 after adding methanolic hydrochloric acid and Pd-on-BaSO$_4$. When the reaction is complete the catalyst is filtered off and the filtrate is concentrated. The resulting oil is triturated with 500 ml of ether and kept cool for several days. The substance crystallizes and is then filtered off. Yield 77.1 g, melting point 148°–150° C., $[\alpha]_D^{25} = -22.1°$ (c=1, in water).

(C) H-Glu-Ile-Val-OBu$^t$ 37 g of Z-Glu(OBzl)OH are reacted with 32 g of H-Ile-Val-OBu$^t$.HCl and the product is worked up, as described in Example 21 (C). After catalytic hydrogenation the compound is a single substance according to chromatography.

(D) Lys-Lys-Glu-Ile-Val-OBu$^t$ acetate 6.8 g of Z-Lys(Z)-Lys(Z)-OH are preactivated in accordance with Example 21 (D) and reacted with 4.15 g of the compound obtained as above. The protective groups are split off and the product is purified analogously to Example 21 D. Yield 4.9 g. Aminoacid analysis: Glu 1.00, Val 0.88, Ile 0.86 and Lys 2.04.

EXAMPLE 24

Lys-Lys-Glu-Ile-Phe-OBu$^t$ acetate (A) Z-Ile-Phe-OBu$^t$ 1.3 ml of N-ethylmorpholine are added to the solution of 2.65 g of Z-Ile-OH, 2.58 g of H-Phe-OBu$^t$ and 1.35 g of HOBt in 30 ml of dimethylformamide and 2.2 g of DCC are added to 0° C. The mixture is allowed to stand for 1 hour at 0° C. and overnight at room temperature. On the following day the precipitate is filtered off and the filtrate is concentrated. The residue is partitioned between ethyl acetate and water. The ethyl acetate phase is extracted by shaking with 20 ml of saturated NaHCO$_3$ solution, 20 ml of K$_2$SO$_4$/KHSO$_4$ solution and 20 ml of NaHCO$_3$ solution and is dried over Na$_2$SO$_4$ and concentrated. The product crystallizes from petroleum ether. Yield 3.7 g, melting point 122°–125°.

(B) H-Ile-Phe-OBu$^t$.HCl 3.65 g of Z-Ile-Phe-OBu$^t$ are dissolved in 100 ml of methanol and subjected to catalytic hydrogenation at pH 4.5 after adding Pd-on-BaSO$_4$ and 2 N methanolic hydrochloric acid. After the reaction is complete the catalyst is filtered off and the filtrate is concentrated. The residue crystallizes on being triturated with ether. Yield 2.57 g, melting point 107°–109°, $[\alpha]_D^{24} = +15.9°$ (c=1, in methanol).

(C) H-Glu-Ile-Phe-OBu$^t$ 1.85 g of Z-Glu(OBzl)-OH, 1.85 g of H-Ile-Phe-OBu$^t$.HCl and 1.1 g of DCC are reacted, analogously to Example 21 (C), in the presence of 0.65 ml of N-ethylmorpholine and 0.7 g of HOBt in dimethylformamide, the product is subjected to catalytic hydrogenation and 2.4 g of the compound insoluble in ether are isolated.

(D) Lys-Lys-Glu-Ile-Phe-OBu$^t$ acetate 3.4 g of Z-Lys(Z)-Lys(Z)-OH are preactivated analogously to Example 21 (D) and reacted with 2.3 g of the compound obtained above. The product is worked up as described in Example 21 (D). Yield 2.5 g. Aminoacid analysis: Glu 1.00, Ile 0.87, Phe 0.97 and Lys 1.98.

EXAMPLE 25

Arg-Lys-Glu-Val-Tyr-OMe diacetate (A) Z-Val-Tyr(Bu$^t$)-OMe 19.5 ml (approx. 150 mmoles) of N-ethylmorpholine and 33 g (160 mmoles) of DCC are added at 0° C. to a solution in 250 ml of dimethylformamide of 43.15 g (150 mmoles) of H-Tyr(Bu$^t$)-OMe.HCl, 37.65 g (150 mmoles) of Z-Val-OH and 20.25 g (150 mmoles) of 1-hydroxybenzotriazole. The mixture is stirred for 1 hour at 0° C. and is allowed to stand overnight at room temperature. The precipitate which has deposited is filtered off. It is rinsed with a little dimethylformamide. The filtrate is introduced into a mixture of 150 ml of saturated NaHCO$_3$ solution and 3,000 ml of water, while stirring. The mixture is cooled to 4° C. and the precipitate is filtered off. It is washed thoroughly with water. While still wet, the product is dissolved in 400 ml of ethyl acetate. Insoluble matter is filtered off and water is separated off in a separating funnel. The ethyl acetate phase is dried over Na$_2$SO$_4$ and concentrated. The residue is triturated with petroleum ether and the product is filtered off. Yield 67 g (92%). Melting point 111°–112°, $[\alpha]_D^{21} = -15.9°$ (c=1, methanol).

(B) H-Val-Tyr(Bu$^t$)-OMe.HCl

Pd-on-charcoal catalyst is added to a solution of 65 g (0.134 mole) of Z-Val-Tyr(Bu$^t$)-OMe in 300 ml of methanol and hydrogen is passed through the solution at pH 4.5 (autotitrator) while stirring and adding approx. 2 N methanolic hydrochloric acid, until no further methanolic hydrochloric acid is taken up. The catalyst is then filtered off and the filtrate is concentrated. The residue is triturated with ether, in the course of which the substance dissolves and, after standing overnight at 4°, precipitates out in crystalline form. The crystals are filtered off and dried over P$_2$O$_5$. The substance is hygroscopic. Yield 44.1 g (85%), melting point 88°–102°, $[\alpha]_D^{21} = +31.0°$ (c=1, methanol).

(C) Z-Glu(OBu$^t$)-Val-Tyr(Bu$^t$)-OMe 14.5 ml (113 mmoles) of N-ethylmorpholine and 58 g (112 mmoles) of Z-Glu(OBu$^t$)-OTcp are added at room temperature to a solution in 120 ml of dimethylformamide of 43.5 g (112.4 mmoles) of H-Val-Tyr(Bu$^t$)-OMe.HCl and 15.1 g (112 mmoles) of 1-hydroxybenzotriazole. The mixture is stirred for two hours at room temperature and the reaction solution is stirred into a mixture of 120 ml of saturated NaHCO$_3$ solution and 1,200 ml of water. The mixture is cooled to 4° C. and the precipitate which has deposited is filtered off. While still wet, the precipitate is dissolved in 1,200 ml of ethyl acetate and the water adhering is removed in a separating funnel. The mixture is extracted once more with 300 ml of water, dried over Na$_2$SO$_4$ and concentrated. The residue is reprecipitated from ethyl acetate/petroleum ether and is dried over paraffin. Yield 70 g (93%), melting point 163°–164°, $[\alpha]_D^{25} = -24.6°$ (c=1, methanol).

(D) H-Glu(OBu$^t$)-Val-Tyr(Bu$^t$)-OMe.HCl 70 g (104 mmoles) of Z-Glu(OBu$^t$)-Val-Tyr(Bu$^t$)-OMe are subjected to catalytic hydrogenation analogously to Example B. The residue does not crystallize and is obtained as an amorphous foam after drying in a high vacuum. Yield 55 g (92.5%), $[\alpha]_D^{21} = +15.3°$ (c=1, methanol).

(E) Z-Lys(Boc)-Glu(OBu$^t$)-Val-Tyr(Bu$^t$)-OMe 6.5 ml (approx. 51 mmoles) of N-methylmorpholine and 28 g (50 mmoles) of Z-Lys(Boc)-OTcp are added at room temperature to a solution in 80 ml of dimethylformamide of 28.6 g (50 mmoles) of H-Glu(OBu$^t$)-Val-Tyr(Bu$^t$)-OMe and 6.75 g (50 mmoles) of 1-hydroxybenzotriazole. The reaction solution is stirred for two hours at room temperature and is introduced into a mixture of 50 ml of saturated NaHCO$_3$ solution and 600 ml of water. The mixture is cooled to 4° C. and the precipitate which has deposited is filtered off. While still wet, the precipitate is dissolved in the necessary quantity of ethyl acetate and the water adhering is separated off in a separating funnel. The ethyl acetate phase is dried over Na$_2$SO$_4$ and concentrated nearly to dryness. The peptide is precipitated from the concentrated solution by means of petroleum ether. The precipitate is filtered off, washed with petroleum ether and dried over paraffin. Yield 44.3 g (98%), melting point 149°-152°, $[\alpha]_D^{21} = -20.4°$ (c=1, methanol).

(F) H-Lys(Boc)-Glu(OBu$^t$)-Val-Tyr(Bu$^t$)-OMe.HCl 44 g (49 mmoles) of Z-Lys(Boc)-Glu(OBu$^t$)-Val-Tyr(Bu$^t$)-OMe are subjected to catalytic hydrogenation analogously to Example B. The residue is triturated with ether. Yield 31.8 g (81%), melting point 175°-177°, $[\alpha]_D^{22} = -10.7°$ (c=1, methanol).

(G) Z-Arg(Z$_2$)-Lys(Boc)-Glu(OBu$^t$)-Val-Tyr(Bu$^t$)-OMe 4.55 ml (35.5 mmoles) of N-ethylmorpholine and a solution of 26.5 g (35 mmoles) of Z-Arg(Z$_2$)-OTcp in 50 ml of dimethylformamide are added at room temperature to a solution of 28 g (35 mmoles) of H-Lys(Boc)-Glu(OBu$^t$)-Val-Tyr(Bu$^t$)-OMe.HCl and 4.73 g of 1-hydroxybenzotriazole in 85 ml of dimethylformamide. The mixture is stirred for two hours at room temperature and is introduced into a mixture of 35 ml of saturated NaHCO$_3$ solution and 700 ml of water. The mixture is cooled to 4° C. and the precipitate is filtered off and dried over P$_2$O$_5$. The substance (44 g) is then boiled up with 1,000 ml of ethyl acetate, 1,000 ml of petroleum ether are added and the mixture is cooled. The precipitate is filtered off and dried. Yield 43.15 g. The substance is purified further by being boiled up with 450 ml of methanol. The mixture is allowed to cool to room temperature and the precipitate is filtered off, rinsed with methanol and dried in vacuo. Yield 38.4 g (81%), melting point 201° C., $[\alpha]_D^{22} = -4.7°$ (c=1, glacial acetic acid).

(H) Z-Arg(Z$_2$)-Lys-Glu-Val-Tyr-OMe 36 g (26.7 mmoles) of Z-Arg(Z$_2$)-Lys(Boc)-Glu(OBu$^t$)-Val-Tyr(Bu$^t$)-OMe are dissolved in 180 ml of 90 percent strength trifluoroacetic acid. The mixture is allowed to stand for 1 hour at room temperature and is concentrated in vacuo. The residue is triturated with water, filtered off and dried. The substance thus obtained is then boiled up with 500 ml of methanol, the mixture is cooled to room temperature and the precipitate is filtered off and dried. Yield 18.1 g (61%), melting point 196°-199° with decomposition, $[\alpha]_D^{21} = -2.8°$ (c=1, dimethylacetamide). The methanol mother liquor is concentrated and the residue is triturated with water, filtered off and dried over P$_2$O$_5$. Yield 10.8 g (36.5%), melting point 187°-191° with decomposition, $[\alpha]_D^{21} = -3.3°$ (c=1, dimethylacetamide). Total yield: 97.5%.

(I) Arg-Lys-Glu-Val-Tyr-OMe acetate 17.5 g (15.8 mmoles) of Z-Arg(Z$_2$)-Lys-Glu-Val-Tyr-OMe are dissolved in 700 ml of 90 percent strength acetic acid. Pd-on-charcoal catalyst is added to the solution and hydrogen is passed through the solution until no further CO$_2$ is evolved. The catalyst is filtered off, the filtrate is concentrated and the residue is dissolved in water. The aqueous solution is filtered, if necessary, and freeze-dried. Yield 12.13 g (92%), $[\alpha]_D^{22} = -35.8°$ (c=1, in water). Aminoacid analysis: Glu (1.00), Val (0.96), Tyr (0.91), Lys (1.04) and Arg (0.95), (hydrolysis: 24 hours at 120° in 6 N HCl).

EXAMPLE 26

Arg-Lys-Glu-Val-Tyr-OH acetate

(A) Z-Val-Tyr(Bu$^t$)-OBu$^t$ 13 ml (approx. 0.1 mole) of N-ethylmorpholine and 22 g (107 mmoles) of dicyclohexylcarbodiimide are added at 0° C. to a solution in 150 ml of dimethylformamide of 33 g (0.1 mole) of H-Tyr(Bu$^t$)-OBu$^t$, 25.1 g (0.1 mole) of Z-Val-OH and 13.5 g of 1-hydroxybenzotriazole. The mixture is stirred for one hour at 0° C. and allowed to stand overnight at room temperature. The precipitate is filtered off and the filtrate is concentrated. The residue is partitioned between 300 ml of ethyl acetate and 300 ml of water. The ethyl acetate phase is extracted by shaking successively with 100 ml of saturated NaHCO$_3$ solution, 100 ml of KHSO$_4$/K$_2$SO$_4$ solution, 100 ml of saturated NaHCO$_3$ solution and 100 ml of water. After drying over Na$_2$SO$_4$ the solution is concentrated. The residue is triturated with petroleum ether, cooled and filtered off. Yield 31.2 g (60%), melting point 82°-83°, $[\alpha]_D^{21} = -20.9°$ (c=1, methanol).

(B) H-Val-Tyr(Bu$^t$)-OBu$^t$.HCl

Pd-on-charcoal catalyst is added to a solution of 31 g (58.8 mmoles) of Z-Val-Tyr(Bu$^t$)-OBu$^t$ in 300 ml of methanol and hydrogen is passed through the solution at pH 4.5 (autotitrator) while stirring and adding approx. 2 N methanolic hydrochloric acid, until no further methanolic hydrochloric acid is taken up. The catalyst is then filtered off and the filtrate is concentrated. The residue is triturated with ether, filtered off and dried. Yield 23.6 g (94%), melting point 159°-161°, $[\alpha]_D^{20} = +19.4°$ (c=1, methanol).

(C) Z-Glu(OBu$^t$)-Val-Tyr(Bu$^t$)-OBu$^t$ 2.6 ml (approx. 20 mmoles) of N-ethylmorpholine and 11.35 g (22 mmoles) of Z-Glu(OBu$^t$)-OTcp are added at room temperature to a solution of 8.6 g (20 mmoles) of H-Val-Tyr(Bu$^t$)-OBu$^t$.HCl and 2.7 g (20 mmoles) of 1-hydroxybenzotriazole in 20 ml of dimethylformamide. The reaction solution is stirred for 2 hours at room temperature and introduced into a mixture of 30 ml of saturated NaHCO$_3$ solution and 200 ml of water. The mixture is cooled to 4° C. and the water is decanted off. The residue is dissolved in 100 ml of ethyl acetate. The ethyl acetate phase is extracted by shaking with 30 ml of KHSO$_4$/K$_2$SO$_4$ solution and with 50 ml of saturated NaHCO$_3$ solution, is dried over Na$_2$SO$_4$ and is concentrated. The residue is dissolved in petroleum ether and is kept overnight at 4° C. A white crystalline substance is precipitated and is filtered off. Yield 3.94 g, melting point 133°. The mother liquor is concentrated and the resulting oil (17.6 g) is chromatographed over 200 g of silica gel. Elution is carried out first with methylene chloride and finally with a mixture, such as 9:1, of methylene chloride and acetone. The fractions which are identical in TLC with the precipitate described above are concentrated and the residue is triturated with a little petroleum ether and filtered off. Yield 7.74 g, melting point 133°, $[\alpha]_D^{25} = -29.4°$ (c=1, methanol). Total yield: 11.68 g (82%).

(D) H-Glu(OBu$^t$)-Val-Tyr(Bu$^t$)-OBu$^t$.HCl 9 g (12.65 mmoles) of Z-Glu(OBu$^t$)-Val-Tyr(Bu$^t$)-OBu$^t$ are subjected to catalytic hydrogenation analogously to Example B. The residue does not crystallize and is obtained as an amorphous foam after drying in a high vacuum. Yield 7.65 g (98.6%), melting point 109°–112°, $[\alpha]_D^{25} = +2.4°$ (c=1, methanol).

(E) Z-Lys(Boc)-Glu(OBu$^t$)-Val-Tyr(Bu$^t$)-OBu$^t$ 0.65 ml (approx. 5 mmoles) of N-ethylmorpholine and a solution of 3.05 g (5.45 mmoles) of Z-Lys(Boc)-OTcp in 10 ml of dimethylformamide are added at room temperature to a solution of 3.07 g (5 mmoles) of H-Glu(OBu$^t$)-Val-Tyr(Bu$^t$)-OBu$^t$.HCl and 675 mg (5 mmoles) of 1-hydroxybenzotriazole in 10 ml of dimethylformamide. The reaction solution is stirred for 2 hours at room temperature and introduced into a mixture of 5 ml of saturated NaHCO$_3$ solution and 200 ml of water. The mixture is cooled to 4° C. and the precipitate is filtered off. The precipitate is dried over P$_2$O$_5$ and is then triturated thoroughly with petroleum ether, filtered off and dried again. Yield 4.7 g (100%), melting point 104°–106°, $[\alpha]_D^{24} = -27.5°$ (c=1, methanol).

(F) H-Lys(Boc)-Glu(OBu$^t$)-Val-Tyr(Bu$^t$)-OBu$^t$.HCl 4.6 g (4.9 mmoles) of Z-Lys(Boc)-Glu(OBu$^t$)-Val-Tyr(Bu$^t$)-OBu$^t$ are subjected to catalytic hydrogenation analogously to Example B. The residue is triturated with ether, filtered off and dried. Yield 3.56 g (86%), melting point 143°–145° with decomposition, $[\alpha]_D = -19.5°$ (c=1, methanol).

(G) Z-Arg(Z$_2$)-Lys(Boc)-Glu(OBu$^t$)-Val-Tyr(Bu$^t$)-OBu$^t$ 0.26 ml (2 mmoles) of N-ethylmorpholine and a solution of 1.66 g (2.2 mmoles) of Z-Arg(Z$_2$)-OTcp in 2 ml of dimethylformamide are added to a solution of 1.68 g (2 mmoles) of H-Lys(Boc)-Glu(OBu$^t$)-Val-Tyr(Bu$^t$)-OBu$^t$.HCl and 270 mg (2 mmoles) of 1-hydroxybenzotriazole in 5 ml of dimethylformamide. The mixture is stirred for two hours at room temperature and a mixture of 5 ml of saturated NaHCO$_3$ solution and 50 ml of water is then added, the combined mixture is cooled to 4° C. and the precipitate is filtered off and dried in vacuo over P$_2$O$_5$. The substance is then triturated with a mixture of 20 ml of ethyl acetate and 30 ml of petroleum ether. The substance is filtered off, washed with petroleum ether and dried. Yield 2.38 g (87%), melting point 185°–187° with decomposition, $[\alpha]_D = -5.4°$ (c=1, dimethylacetamide).

(H) H-Arg-Lys(Boc)-Glu(OBu$^t$)-Val-Tyr(Bu$^t$)-OBu$^t$.2HCl 2.2 g (1.61 mmoles) of Z-Arg(Z$_2$)-Lys(Boc)-Glu(OBu$^t$)-Val-Tyr(Bu$^t$)-OBu$^t$ are subjected to catalytic hydrogenation analogously to Example B. The residue is triturated with ether and filtered off. Yield 1.4 g (84%). $[\alpha]_D = -17.7°$ (c=1, methanol).

(I) H-Arg-Lys-Glu-Val-Tyr-OH acetate 1 g of H-Arg-Lys(Boc)-Glu(OBu$^t$)-Val-Tyr(Bu$^t$)-OBu$^t$.2HCl (0.966 mmole) is dissolved in a mixture of 10 ml of trifluoroacetic acid and 1 ml of ethylmercaptan. The mixture is allowed to stand for one hour at room temperature and is concentrated. The residue is dissolved again in a little methanol and the solution is concentrated once more. The residue is dissolved in water, insoluble matter is filtered off and the solution is chromatographed over a strongly basic exchanger in the acetate form. The eluate is concentrated and purified further by being chromatographed on a hydroxypropylated crosslinked dextran gel in a water/acetic acid/n-butanol mixture. Yield 491 mg (57%), $[\alpha]_D = -21.8°$ (c=1, water). Aminoacid analysis: Glu 1.00, Val 0.97, Tyr 0.92, Lys 1.03 and Arg 0.99. Protein content: 82%.

EXAMPLE 27

Lys-Arg-Glu-Val-Tyr-OMe acetate (A) Z-Arg(Z$_2$)-Glu(OBu$^t$)-Val-Tyr(Bu$^t$)-OMe 2.6 ml (20 mmoles) of N-ethylmorpholine and 15.12 g (20 mmoles) of Z-Arg(Z$_2$)-OTcp are added at room temperature to a solution of 11.4 g (20 mmoles) of H-Glu(OBu$^t$)-Val-Tyr(Bu$^t$)-OMe.HCl and 2.7 g (20 mmoles) of 1-hydroxybenzotriazole in 40 ml of dimethylformamide. The mixture is stirred for two hours at room temperature. It is then stirred with 400 ml of water and 20 ml of saturated NaHCO$_3$ solution. The precipitate is filtered off and dried. It is recrystallized from hot ethyl acetate. Yield 20 g (91%). Melting point 186°–188°, $[\alpha]_D^{22} = -0.9°$ (c=1, in glacial acetic acid).

(B) H-Arg-Glu(OBu$^t$)-Val-Tyr(Bu$^t$)-OMe.2HCl 18.5 g (16.9 mmoles) of Z-Arg(Z$_2$)-Glu(OBu$^t$)-Val-Tyr(Bu$^t$)-OMe are subjected to catalytic hydrogenation and the product is worked up analogously to Example 26 B. Yield 11.5 g (89%), melting point 149°–150°, $[\alpha]_D^{22} = -9.2°$ (c=1, in methanol).

(C) Z-Lys(Boc)-Arg-Glu(OBu$^t$)-Val-Tyr(Bu$^t$)-OMe.HCl 0.26 ml of N-ethylmorpholine and 1.12 g (2 mmoles) of Z-Lys(Boc)-OTcp are added at room temperature to a solution of 1.53 g (2 mmoles) of H-Arg-Glu(OBu$^t$)-Val-Tyr(Bu$^t$)-OMe.2HCl and 0.27 g (2 mmoles) of 1-hydroxybenzotriazole in 8 ml of dimethylformamide. The mixture is stirred for two hours at room temperature and 30 ml of water and 2 ml of saturated NaHCO$_3$ solution are then added. The precipitate is filtered off and dried. It is purified by being reprecipitated twice from 1:1 ethyl acetate/petroleum ether. Yield 1.44 g (66%). Melting point 117°–119° with decomposition, $[\alpha]_D^{22} = -24.5°$ (c=1, in methanol).

(D) Z-Lys-Arg-Glu-Val-Tyr-OMe acetate 1.2 g (1.1 mmoles) of Z-Lys(Boc)-Arg-Glu(OBu$^t$)-Val-Tyr(Bu$^t$)-OMe.HCl are dissolved in 10 ml of 90 percent strength trifluoroacetic acid. The mixture is allowed to stand for one hour at room temperature and is concentrated. The residue is partitioned between 150 ml of water and 100 ml of diethyl ether. The aqueous phase is stirred with a weakly basic ion exchanger in the acetate form. The exchanger is filtered off and the filtrate is freeze-dried. Yield 880 mg (89%), $[\alpha]_D^{23} = -45.8°$ (c=1, in water).

(E) Lys-Arg-Glu-Val-Tyr-OMe acetate 800 mg (approx. 0.88 mmole) of Z-Lys-Arg-Glu-Val-Tyr-Ome acetate are subjected to catalytic hydrogenation in 90 percent strength acetic acid and the product is worked up analogously to Example 25 I. Yield 680 mg (93%), $[\alpha]_D^{22} = -31.6°$ (c=1, in water).

EXAMPLE 28

D-Lys-Arg-Glu-Val-Tyr-OMe acetate (A)
Z-D-Lys(Boc)-Arg-Glu(OBu$^t$)-Val-Tyr(Bu$^t$)-OMe.HCl 0.54 g (4 mmoles) of N-ethylmorpholine and 2.24 g (4 mmoles) of Z-D-Lys(Boc)-OTcp are added at room temperature to a solution of 3.06 g (4 mmoles) of H-Arg-Glu(OBu$^t$)-Val-Tyr(Bu$^t$)-OMe.2HCl and 0.54 g (4 mmoles) of HOBt in 16 ml of dimethylformamide. The product is worked up analogously to Example 27 C. Yield 4.0 g (92%), melting point 167°–172°, $[\alpha]_D^{22} = -15.5°$ (c=1, methanol).

(B) Z-D-Lys-Arg-Glu-Val-Tyr-OMe acetate 3.6 g (3.3 mmoles) of Z-D-Lys(Boc)-Arg-Glu(OBu$^t$)-Val-Tyr(Bu$^t$)-OMe.HCl are dissolved in 30 ml of 90 percent strength trifluoroacetic acid and the product is worked up analogously to Example 27 D. Yield 2.81 g (94%), $[\alpha]_D^{23} = -32.4°$ (c=1, water).

(C) D-Lys-Arg-Glu-Val-Tyr-OMe acetate 2 g (2.2 mmoles) of Z-D-Lys-Arg-Glu-Val-Tyr-OMe acetate are subjected to catalytic hydrogenation in 90 percent acetic acid and the product is worked up analogously to Example 25 I. Yield 1.8 g (98%). 800 mg are purified further by being chromatographed on a hydroxypropylated, crosslinked dextran gel (approx. 120 g, column: 90×2.5 cm) in 90 percent strength methanol. Yield 500 mg.

EXAMPLE 29

Arg-Lys-Glu-Val-Trp-OMe acetate (A) Z-Val-Trp-OMe 6.5 ml (approx. 50 mmoles) of N-ethylmorpholine and 11 g of dicyclohexylcarbodiimide are added at 0° C. to a solution in 100 ml of dimethylformamide of 12.64 g (50 mmoles) of H-Trp-OMe.HCl, 6.75 g (50 mmoles) of 1-hydroxybenzotriazole and 12.55 g (50 mmoles) of Z-Val-OH. The mixture is stirred for one hour at 0° C. and is allowed to stand overnight at room temperature. On the following day the precipitate is filtered off and the filtrate is stirred with 50 ml of saturated NaHCO$_3$ solution and 1,000 ml of water. The mixture is cooled to 4° C. and the precipitate is filtered off. While still wet, the precipitate is dissolved in ethyl acetate. The ethyl acetate phase is extracted by shaking with water, saturated NaHCO$_3$ solution, KHSO$_4$/K$_2$SO$_4$ solution and again with saturated NaHCO$_3$ solution and is dried over Na$_2$SO$_4$ and concentrated to a small residue. The peptide is precipitated from the concentrated solution with petroleum ether. The precipitate is filtered off and dried. Yield 19.1 g (84%), melting point 146°–148°, $[\alpha]_D^{22} = -13.9°$ (c=1, in methanol).

(B) H-Val-Trp-OMe.HCl 18.2 g (40.3 mmoles) of Z-Val-Trp-OMe are subjected to catalytic hydrogenation analogously to Example 25 B. The substance crystallizes from ether. Yield 12.9 g (90%), melting point 218°–221°, $[\alpha]_D^{22} = +14.2°$ (c=1, in methanol).

(C) Z-Glu(OBu$^t$)-Val-Trp-OMe 4.38 ml (34.2 mmoles) of N-ethylmorpholine and 17.7 g (34.2 mmoles) of Z-Glu(OBu$^t$)-OTcp are added at room temperature to a solution of 12.1 g (34.2 mmoles) of H-Val-Trp-OMe.HCl and 4.62 g (34.2 mmoles) of 1-hydroxybenzotriazole in 50 ml of dimethylformamide. The solution is stirred for 2 hours at room temperature and 35 ml of saturated NaHCO$_3$ solution and 350 ml of water are then added to it. The mixture is cooled to 4° C. and the precipitate is filtered off. The moist substance is dissolved in ethyl acetate. The ethyl acetate phase is extracted with 100 ml of water, dried over Na$_2$SO$_4$ and concentrated. The residue is triturated with petroleum ether and filtered off. Yield 20.5 g (94%), melting point 158°–162°, $[\alpha]_D^{22} = -26.1°$ (c=1, in methanol).

(D) H-Glu(OBu$^t$)-Val-Trp-OMe.HCl 19.8 g (31 mmoles) of Z-Glu(OBu$^t$)-Val-Trp-OMe are subjected to catalytic hydrogenation analogously to Example 25 B. The substance is amorphous. Yield 15.3 g (91%), $[\alpha]_D^{22} = +9.5°$ (c=1, in methanol).

(E) Z-Lys(Boc)-Glu(OBu$^t$)-Val-Trp-OMe 3.45 ml (26.9 mmoles) of N-ethylmorpholine and 15.06 g (26.9 mmoles) of Z-Lys(Boc)-OTcp are added to a solution of 14.5 g (26.9 mmoles) of H-Glu(OBu$^t$)-Val-Trp-OMe and 3.63 g (26.9 mmoles) of 1-hydroxybenzotriazole in 60 ml of dimethylformamide. The mixture is stirred for two hours at room temperature and 25 ml of saturated NaHCO$_3$ solution and 300 ml of water are then added, while cooling. The precipitate is filtered off and dried. The residue is triturated with petroleum ether and filtered off. It is purified further by recrystallization from ethyl acetate. Yield 19.3 g (83%), melting point 169°–174°, $[\alpha]_D^{22} = -28.1°$ (c=1, in methanol).

(F) H-Lys(Boc)-Glu(OBu$^t$)-Val-Trp-OMe.HCl 6.3 g (7.28 mmoles) of Z-Lys-(Boc)-Glu(OBu$^t$)-Val-Trp-OMe are subjected to catalytic hydrogenation analogously to Example 25 B. Yield 4.8 g (86%), melting point 158°–162°, $[\alpha]_D^{23} = -16.2°$ (c=1, in methanol).

(G) Z-Arg(Z$_2$)-Lys(Boc)-Glu(OBu$^t$)-Val-Trp-OMe 0.75 ml (5.86 mmoles) of N-ethylmorpholine and 4.44 g (5.87 mmoles) of Z-Arg(Z$_2$)-OTcp are added at room temperature to a solution of 4.5 g (5.87 mmoles) of H-Lys(Boc)-Glu(OBu$^t$)-Val-Trp-Ome.HCl and 0.8 g (approx. 5.9 mmoles) of 1-hydroxybenzotriazole in 70 ml of dimethylformamide. The mixture is stirred for two hours at room temperature and 5.9 ml of saturated NaHCO$_3$ solution and 700 ml of water are then added. The precipitate is filtered off and dried. Yield 7.4 g. The substance is purified further by being boiled up with 70 ml of methanol, the solution is cooled to room temperature and the precipitate is filtered off. Yield 6.6 g (87%), melting point 189°–190°, $[\alpha]_D^{20} = -4.7°$ (c=1, in glacial acetic acid).

(H) Z-Arg(Z$_2$)-Lys-Glu-Val-Trp-OMe 5 g (3.88 mmoles) of Z-Arg(Z$_2$)-Lys(Boc)-Glu(OBu$^t$)-Val-Trp-OMe are dissolved in 30 ml of trifluoroacetic acid together with 1.2 ml of ethanedithiol. After standing for one hour at room temperature, the solution is concentrated and the residue is digested several times with water, filtered off and dried. It is then boiled up with twice 30 ml of ethyl acetate and the precipitate is filtered off and dried. Yield 3.97 g (90%). The substance is purified further by being chromatographed on silica gel in a mixture of the solvents methylene chloride:methanol:water:acetic acid in a ratio such as 90:15:2:2. Yield 2.78 g (63%). The amorphous residue was processed further without being characterized.

(I) H-Arg-Lys-Glu-Val-Trp-OMe diacetate 1.4 g (1.23 mmoles) of Z-Arg(Z$_2$)-Lys-Glu-Val-OMe are dissolved in 70 ml of 90 percent strength aqueous acetic acid. Palladium catalyst is added and hydrogen is passed through the solution until $CO_2$ is no longer evolved. The catalyst is then filtered off and the filtrate is concentrated. The residue is dissolved in water and the solution is filtered and freeze-dried. Yield 580 mg (55%). Further purification is carried out by chromatographing 500 mg on a hydroxypropylated dextran gel (100×2.5 cm) in 90 percent strength aqueous methanol. Yield 215 mg.

EXAMPLE 30

Arg-Lys-Glu-Val-Tyr-O-cyclohexyl acetate

(A) Z-Tyr(Bu$^t$)-O-cyclohexyl 20 ml of a 50 percent strength solution of propylphosphonic anhydride in methylene chloride are added at 5° C., in the course of 15 minutes and while stirring, to a solution of 9.27 g (25 mmoles) of Z-Tyr(Bu$^t$)-OH in 15 ml of pyridine and 30 ml of cyclohexanol. When the addition is complete, the mixture is allowed to come to room temperature and is left to stand overnight at room temperature. The mixture is partitioned between diisopropyl ether and water. The organic phase is extracted by shaking successively with KHSO$_4$ solution, NaHCO$_3$ solution and water, dried over Na$_2$SO$_4$ and concentrated. 20.8 g of a colorless oil are left as residue. The substance is purified further by being chromatographed over 150 g of silica gel in a 9:1 methylene chloride/acetone mixture. Yield 12.2 g of a colorless oil (still containing solvent).

(B) H-Tyr(Bu$^t$)-O-cyclohexyl.HCl 24.5 g of oily Z-Tyr(Bu$^t$)-O-cyclohexyl, still containing methylene chloride, (at most 50 mmoles) are subjected to catalytic hydrogenation in 350 ml of methanol analogously to Example 25B. The residue is triturated with petroleum ether, filtered off and dried. Yield 15.9 g (91%), melting point 181°, with decomposition, $[\alpha]_D^{22} = +17.8°$ (c=1, in methanol).

(C) Z-Val-Tyr(Bu$^t$)-O-cyclohexyl 2.5 ml (approx. 20 mmoles) of N-ethylmorpholine and 4.4 g (21.5 mmoles) of dicyclohexylcarbodiimide are added at 0° C. to a solution in 20 ml of dimethylformamide of 5.03 g (20 mmoles) of Z-Val-OH, 7 g (20 mmoles) of H-Tyr(Bu$^t$)-O-cyclohexyl.HCl and 2.7 g (20 mmoles) of 1-hydroxybenzotriazole. The mixture is stirred for 1 hour at 0° C. and then overnight at room temperature. The precipitate is filtered off and 200 ml of water and 20 ml of saturated NaHCO$_3$ solution are added to the filtrate. The precipitate is filtered off and washed with water. While still wet with water, the product is partitioned between 150 ml of ethyl acetate and 150 ml of water. The ethyl acetate phase is washed once more with 100 ml of saturated NaHCO$_3$ solution, dried over Na$_2$SO$_4$ and concentrated. The residue is triturated with petroleum ether and filtered off. Yield 7.25 g (65%), melting point 99°–100°, $[\alpha]_D^{23} = -23.3°$ (c=1, in methanol).

(D) H-Val-Tyr(Bu$^t$)-O-cyclohexyl.HCl 6.5 g (11.76 mmoles) of Z-Val-Tyr(Bu$^t$)O-cyclohexyl are subjected to catalytic hydrogenation in 150 ml of methanol analogously to Example 25 B. The residue is triturated with ether, cooled, filtered off and dried. Yield 5.35 g (100%), melting point 152°–154°, $[\alpha]_D^{22} = +20.4°$ (c=1, in methanol).

(E) Z-Glu(OBu$^t$)-Val-Tyr(Bu$^t$)-O-cyclohexyl 1.3 ml (10 mmoles) of N-ethylmorpholine and 5.2 g (10 mmoles) of Z-Glu(OBu$^t$)-OTcp are added at 0° to a solution of 4.6 g (10 mmoles) of H-Val-Tyr(Bu$^t$)-O-cyclohexyl hydrochloride and 1.35 g of 1-hydroxybenzotriazole in 20 ml of dimethylformamide. The mixture is stirred for two hours at room temperature and a mixture of 200 ml of water and 20 ml of saturated NaHCO$_3$ solution is then added, while stirring. The precipitate is filtered off and washed with water. While still wet, the precipitate is dissolved in 200 ml of ethyl acetate. The water adhering is separated off. The ethyl acetate phase is extracted by shaking once more with 50 ml of water, dried over Na$_2$SO$_4$ and concentrated. The product is reprecipitated from ethyl acetate/petroleum ether. The precipitate is filtered off, washed with petroleum ether and dried. Yield 5.4 g (73%), melting point 160°–162°, $[\alpha]_D^{24} = -28.3°$ (c=1, in methanol).

(F) H-Glu(OBu$^t$)-Val-Tyr(Bu$^t$)-O-cyclohexyl.HCl 4.5 g (6.1 mmoles) of Z-Glu(OBu$^t$)-Val-Tyr(Bu$^t$)-O-cyclohexyl are subjected to catalytic hydrogenation in 250 ml of methanol analogously to Example 25 B. The residue is 3.2 g (82%) of an amorphous foam, which is processed further without being characterized.

(G) Z-Lys(Boc)-Glu(OBu$^t$)-Val-Tyr(Bu$^t$)-O-cyclohexyl 0.65 ml (5 mmoles) of N-ethylmorpholine and 2.8 g (5 mmoles) of Z-Lys(Boc)-OTcp are added at room temperature to a solution of 3.2 g (5 mmoles) of H-Glu(OBu$^t$)-Val-Tyr(Bu$^t$)-O-cyclohexyl.HCl and 675 mg (5 mmoles) of 1-hydroxybenzotriazole in 10 ml of dimethylformamide. The mixture is stirred for two hours at room temperature and the product is worked up analogously to E. Yield 3.5 g (72%), melting point 141°–145°, $[\alpha]_D^{24} = -28.0°$ (c=1, in methanol).

(H) H-Lys(Boc)-Glu(OBu$^t$)-Val-Tyr(Bu$^t$)-O-cyclohexyl.HCl 3 g (3.1 mmoles) of Z-Lys(Boc)-Glu(OBu$^t$)-Val-Tyr(Bu$^t$)-O-cyclohexyl are subjected to catalytic hydrogenation in 150 ml of methanol analogously to Example 25 B. The residue is triturated with ether, filtered off and dried. Yield 2.47 g (92%), melting point 184°–186°, $[\alpha]_D^{24}=-15.4°$ (c=1, in methanol).

(I) Z-Arg(Z$_2$)-Lys(Boc)-Glu(OBu$^t$)-Val-Tyr(Bu$^t$)-O-cyclohexyl 0.3 ml (2.3 mmoles) of N-ethylmorpholine and a solution of 1.74 g (2.3 mmoles) of Z-Arg(Z$_2$)-OTcp in 3 ml of dimethylformamide are added at room temperature to a solution of 2.0 g (2.3 mmoles) of H-Lys(Boc)-Glu(OBu$^t$)-Val-Tyr(Bu$^t$)-O-cyclohexyl.HCl and 310 mg (2.3 mmoles) of 1-hydroxybenzotriazole in 8 ml of dimethylformamide. The mixture is then stirred for two hours at room temperature and 3 ml of saturated NaHCO$_3$ solution and 50 ml of water are added. The precipitate is filtered off and dried. The substance is purified by being dissolved in hot ethyl acetate and precipitated with petroleum ether. The precipitate is filtered off, washed with petroleum ether and dried. Yield 3 g (94%), melting point 184°–185°, $[\alpha]_D^{24}=-9.2°$ (c=1, in glacial acetic acid).

(K) Z-Arg(Z$_2$)-Lys-Glu-Val-Tyr-O-cyclohexyl 2.5 g (1.8 mmoles) of Z-Arg(Z$_2$)-Lys(Boc)-Glu(OBu$^t$)-Val-Tyr(Bu$^t$)-O-cyclohexyl are dissolved in 12.5 ml of 90 percent strength trifluoroacetic acid. The solution is allowed to stand for one hour at room temperature and is concentrated in vacuo. The residue is triturated with water, filtered off and dried. Yield 2.5 g (the substance still contains trifluoroacetic acid and water). Melting point 167°–171°, $[\alpha]_D^{26}=-15.7°$ (c=1, glacial acetic acid).

(L) Arg-Lys-Glu-Val-Tyr-O-cyclohexyl acetate 2 g (at most 1.44 mmoles) of the Z-Arg(Z$_2$)-Lys-Glu-Val-Tyr-O-cyclohexyl obtained in accordance with Example K are subjected to catalytic hydrogenation in 150 ml of 90 percent strength acetic acid analogously to Example 25 I. The residue is chromatographed in water over a weakly basic ion exchanger in the acetate form (30×2 cm). The eluate containing peptide is freeze-dried. Yield 1.18 g (91%). 800 mg are purified further by being chromatographed on a hydroxypropylated, crosslinked dextran gel in 90 percent strength methanol. Yield 600 mg, $[\alpha]_D^{24}=-48°$ (c=1, water). Aminoacid analysis: Glu (1.00), Val (1.02), Tyr (0.91), Lys (0.99) and Arg (0.99), content of peptide base: 84%.

EXAMPLE 31

Arg-Lys-Glu-Ile-Tyr-O-cyclohexyl acetate (A) Z-Ile-Tyr(Bu$^t$)-O-cyclohexyl 5.8 g (20 mmoles) of Z-Ile-OH and 7 g (20 mmoles) of H-Tyr(Bu$^t$)-O-cyclohexyl.HCl are subjected to a condensation reaction analogously to Example 30 C. Yield 7.7 g (68%), melting point 114°–115°, $[\alpha]_D^{23}=-24.8°$ (c=1, methanol).

(B) H-Ile-Tyr(Bu$^t$)-O-cyclohexyl.HCl 7 g (15.4 mmoles) of Z-Ile-Tyr(Bu$^t$)-O-cyclohexyl are subjected to catalytic hydrogenation in 150 ml of methanol. Yield 5.7 g (79%), melting point 136°–138°, $[\alpha]_D^{22}=+19.5°$ (c=1, methanol).

(C) Z-Glu(OBu$^t$)-Ile-Tyr(Bu$^t$)-O-cyclohexyl 4.7 g (10 mmole) of H-Ile-Tyr(Bu$^t$)-O-cyclohexyl.HCl and 5.2 g (10 mmoles) of Z-Glu(OBu$^t$)-OTcp are subjected to a condensation reaction analogously to Example 30 E. Yield 5.9 g (79%), melting point 164°–165°, $[\alpha]_D^{24}=-28.1°$ (c=1, methanol).

(D) Z-Lys(Boc)-Glu(OBu$^t$)-Ile-Tyr(Bu$^t$)-O-cyclohexyl 5 g (6.65 mmoles) of Z-Glu(OBu$^t$)-Ile-Tyr(Bu$^t$)-O-cyclohexyl are subjected to catalytic hydrogenation in 200 ml of methanol analogously to Example 30 F. Yield 4.3 g (99%).

The 4.3 g (6.6 mmoles) of H-Glu(OBu$^t$)-Ile-Tyr(Bu$^t$)-O-cyclohexyl.HCl obtained above are reacted with 3.7 g (6.6 mmoles) of Z-Lys(Boc)-OTcp analogously to Example 30 G. Yield 4.4 g (68%), melting point 148°–151°, $[\alpha]_D^{24}=-27.8°$ (c=1, in methanol).

(E) H-Lys-(Boc)-Glu(OBu$^t$)-Ile-Tyr(Bu$^t$)-O-cyclohexyl.HCl 4.0 g (4.08 mmoles) of Z-Lys(Boc)-Glu(OBu$^t$)-Ile-Tyr(Bu$^t$)-O-cyclohexyl are subjected to catalytic hydrogenation analogously to Example 30 H. Yield 3.26 g (90%), melting point 179°–180°, $[\alpha]_D^{24}=-17.3°$ (c=1, in methanol).

(F) Z-Arg(Z$_2$)-Lys(Boc)-Glu(OBu$^t$)-Ile-Tyr(Bu$^t$)-O-cyclohexyl 2.5 g (2.83 mmoles) of H-Lys(Boc)-Glu(OBu$^t$)-Ile-Tyr(Bu$^t$)-O-cyclohexyl.HCl are reacted with 2.2 g (2.9 mmoles) of Z-Arg(Z$_2$)-OTcp. Yield 3.9 g (98%), melting point 182°–184°, $[\alpha]_D^{24}=-9.5°$ (c=1, in glacial acetic acid).

(G) Z-Arg(Z$_2$)-Lys-Glu-Ile-Tyr-O-cyclohexyl.

3.5 g (2.5 mmoles) of Z-Arg(Z$_2$)-Lys(Boc)-Glu(OBu$^t$)-Ile-Tyr(Bu$^t$)-O-cyclohexyl are treated with 90 percent strength trifluoroacetic acid analogously to Example 30 K. Yield 3.4 g (the substance still contains trifluoroacetic acid and water), melting point 176°–179°, with decomposition, $[\alpha]_D^{26}=-16.6°$ (c=1, in glacial acetic acid).

(H) H-Arg-Lys-Glu-Ile-Tyr-O-cyclohexyl acetate 3 g (approx. 2.2 mmoles) of Z-Arg(Z$_2$)-Lys-Glu-Ile-Tyr-O-cyclohexyl are subjected to catalytic hydrogenation in 150 ml of 90 percent strength acetic acid and the product is worked up analogously to Example 30 L. Yield 1.675 g (76%). 800 mg are purified further by being chromatographed on a hydroxypropylated, crosslinked dextran gel in 90 percent strength methanol. Yield 560 mg, $[\alpha]_D^{25}=-46.1°$ (c=1, water).

EXAMPLE 32

Arg-Lys-Glu-Val-Tyr-O-n-hexyl acetate (A) Z-Tyr(Bu$^t$)-O-n-hexyl 40 ml of a 50 percent strength solution of propylphosphonic anhydride in methylene chloride are added at 5° C., within the course of 15 minutes and while stirring, to a solution of 18.6 g (50 mmoles) of Z-Tyr(Bu$^t$)-OH in 30 ml of pyridine and 30 ml of n-hexanol. The product is then worked up analogously to Example 30 A. Yield 19.2 g (85%) of a colorless oil.

(B) H-Tyr(Bu$^t$)-O-n-hexyl.HCl 19.2 g (42 mmoles) of oily Z-Tyr(Bu$^t$)-O-n-hexyl are subjected to catalytic hydrogenation in 300 ml of methanol analogously to Example 25 B. The substance crystallizes from diisopropyl ether. Yield 10.11 g (66%).

Melting point 95°–96°, $[\alpha]_D^{24} = +11.7°$ (c=1, methanol).

(C) Z-Val-Tyr(Bu$^t$)-O-n-hexyl 5.37 g (15 mmoles) of H-Tyr(Bu$^t$)-O-n-hexyl hydrochloride and 3.77 g (15 mmoles) of Z-Val-OH are subjected to a condensation reaction analogously to Example 30 C. Yield 6.83 g (82%), melting point 99°, $[\alpha]_D^{23} = -20.3°$ (c=1, methanol).

(D) H-Val-Tyr(Bu$^t$)-O-n-hexyl.HCl 6.5 g (11.7 mmoles) of Z-Val-Tyr(Bu$^t$)-O-n-hexyl are subjected to catalytic hydrogenation analogously to Example 30 D. The substance crystallizes from ether. Yield 5.28 g (98%), melting point 138°–139°, $[\alpha]_D^{23} = +22.4°$ (c=1, methanol).

(E) Z-Glu(OBu$^t$)-Val-Tyr(Bu$^t$)-O-n-hexyl 5.02 g (11 mmoles) of H-Val-Tyr(Bu$^t$)-O-n-hexyl.HCl and 5.93 g (11.5 mmoles) of Z-Glu(OBu$^t$)-OTcp are subjected to a condensation reaction analogously to Example 30 E. Yield 5.65 g (69%), melting point 131°, $[\alpha]_D^{26} = -24.6°$ (c=1, methanol).

(F) H-Glu(OBu$^t$)-Val-Tyr-(Bu$^t$)-O-n-hexyl.HCl 5.2 g (7.03 mmoles) of Z-Glu(OBu$^t$)-Val-Tyr(Bu$^t$)-O-n-hexyl are subjected to catalytic hydrogenation analogously to Example 30 F. The residue is dried at a high temperature. It is soluble in ether. Yield 3.9 g (86%), melting point 105°–110°, $[\alpha]_D^{26} = +7.3°$ (c=1, in methanol).

(G) Z-Lyz(Boc)-Glu(OBu$^t$)-Val-Tyr(Bu$^t$)-O-n-hexyl 3.21 g (5 mmoles) of H-Glu(OBu$^t$)-Val-Tyr(Bu$^t$)-O-n-hexyl.HCl and 3.07 g (5.5 mmoles) of Z-Lys(Boc)-OTcp are subjected to a condensation reaction analogously to Example 30 G. The substance is extracted by boiling with ether and the product is filtered off while warm. Yield 3.87 g (80%), melting point 161°–162°, $[\alpha]_D^{25} = -28.4°$ (c=1, methanol).

(H) H-Lys(Boc)-Glu(OBu$^t$)-Val-Tyr(Bu$^t$)-O-n-hexyl 3.4 g (3.5 mmoles) of Z-Lys(Boc)-Glu(OBu$^t$)-Val-Tyr(Bu$^t$)-O-n-hexyl are subjected to catalytic hydrogenation analogously to Example 30 H. The residue is triturated with ether. Yield 2.68 g (88%), melting point 185°–188°, $[\alpha]_D^{24} = -13.3°$ (c=1, methanol).

(I) Z-Arg(Z$_2$)-Lys(Boc)-Glu(OBu$^t$)-Val-Tyr(Bu$^t$)-O-n-hexyl 2.52 g (2.9 mmoles) of H-Lys(Boc)-Glu(OBu$^t$)-Val-Tyr(Bu$^t$)-O-n-hexyl.HCl are reacted with 2.27 g (3 mmoles) of Z-Arg(Z$_2$)-OTcp analogously to Example 30 I. The substance is heated to boiling with 50 ml of alcohol and the product is filtered off while hot. Yield 3.43 g (85%), melting point 190°, $[\alpha]_D^{23} = -6.7°$ (c=1, dimethylformamide).

(K) Z-Arg(Z$_2$)-Lys-Glu-Val-Tyr-O-n-hexyl 3.1 g (approx. 2.2 mmoles) of Z-Arg(Z$_2$)-Lys(Boc)-Glu(OBu$^t$)-Val-Tyr(Bu$^t$)-O-n-hexyl are treated with 90 percent trifluoroacetic acid analogously to Example 30 K. Yield 2.42 g (93%).

(L) H-Arg-Lys-Glu-Val-Tyr-O-n-hexyl acetate 2.42 g (1.73 mmoles) of Z-Arg(Z$_2$)-Lys-Glu-Val-Tyr-O-n-hexyl are subjected to catalytic hydrogenation in 90 percent acetic acid and the product is worked up analogously to Example 30 L. Yield 1.32 g. 800 mg are purified further by being chromatographed on a hydroxypropylated, crosslinked dextran gel in 90 percent strength methanol. Yield 531.3 mg, $[\alpha]_D^{22} = -43.5°$ (c=1, water).

EXAMPLE 33

Arg-Lys-Glu-Val-Tyr-O-n-butyl acetate (A) Z-Tyr-(Bu$^t$)-O-n-butyl 40 ml of a 50 percent solution of propylphosphonic anhydride in methylene chloride are added at 5° C., in the course of 15 minutes and while stirring, to a solution of 18.6 g (50 mmoles) of Z-Tyr(Bu$^t$)-OH in 30 ml of pyridine and 30 ml of n-butanol. The product is worked up analogously to Example 30 A. Yield 16.6 g (78%) of a colorless oil.

(B) H-Tyr(Bu$^t$)-O-n-butyl.HCl 11 g (25.7 mmoles) of oily Z-Tyr(Bu$^t$)-O-n-butyl are subjected to catalytic hydrogenation analogously to Example 25 B. The substance crystallizes from ether. Yield 6.36 g (72%), melting point 134°, $[\alpha]_D^{22} = +12.4°$ (c=1, methanol).

(C) Z-Val-Tyr(Bu$^t$)-O-n-butyl 6.6 g (20 mmoles) of H-Tyr(Bu$^t$)-O-n-butyl hydrochloride and 5.01 g (20 mmoles) of Z-Val-OH are subjected to a condensation reaction analogously to Example 30 C. Yield 9.73 g (92%). The substance is purified by being chromatographed in a methylene chloride/acetone mixture, such as 9:1, on a silica gel column (100 g). Yield 7.7 g (73%), melting point 91°.

(D) H-Val-Tyr(Bu$^t$)-O-n-butyl.HCl 6.87 g (approx. 13 mmoles) of Z-Val-Tyr(Bu$^t$)-O-n-butyl are subjected to catalytic hydrogenation analogously to Example 30 D. The substance crystallizes from ether. Yield 5.31 g (95%), melting point 113°–115°, with decomposition, $[\alpha]_D^{25} = +4.0°$ (c=1, methanol).

(E) Z-Glu(OBu$^t$)-Val-Tyr(Bu$^t$)-O-n-butyl 5.15 g (12 mmoles) of H-Val-Tyr(Bu$^t$)-O-n-butyl.HCl are reacted with 6.35 g (12.5 mmoles) of Z-Glu(OBu$^t$)-OTcp analogously to Example 30 E. Yield 7.31 g (85%), melting point 155°, $[\alpha]_D^{25} = -25.5°$ (c=1, methanol).

(F) H-Glu(OBu$^t$)-Val-Tyr(Bu$^t$)-O-n-butyl.HCl 7.12 g (10 mmoles) of Z-Glu(OBu$^t$)-Val-Tyr(Bu$^t$)-O-n-butyl are subjected to catalytic hydrogenation analogously to Example 30 F. The residue is dried at a high temperature. It is soluble in ether. Yield 5.96 g (97%), melting point 110°, $[\alpha]_D^{23} = +7.4°$ (c=1, methanol).

(G) Z-Lys(Boc)-Glu(OBu$^t$)-Val-Tyr(Bu$^t$)-O-n-butyl 4.91 g (8 mmoles) of H-Glu(OBu$^t$)-Val-Tyr(Bu$^t$)-O-n-butyl-HCl are reacted with 5.03 g (9 mmoles) of Z-Lys(Boc)-OTcp analogously to Example 30 G. Yield 6.18 g (82%), melting point 146°, $[\alpha]_D^{22} = -28.6°$ (c=1, methanol).

(H) H-Lys(Boc)-Glu(OBu$^t$)-Val-Tyr-(Bu$^t$)-O-n-butyl.HCl 5.65 g (6 mmoles) of Z-Lys(Boc)-Glu(OBu$^t$)-Val-Tyr(Bu$^t$)-O-n-butyl are subjected to catalytic hydrogenation analogously to Examples 30 H. The residue is

(I)
Z-Arg(Z₂)-Lys(Boc)-Glu(OBuᵗ)-Val-Tyr(Buᵗ)O-n-butyl 4.21 g (5 mmoles) of H-Lys(Boc)-Glu(OBu$^t$)-Val-Tyr(Bu$^t$)-O-n-butyl.HCl are reacted with 4.16 g (5.5 mmoles) of Z-Arg(Z₂)-OTcp analogously to Example 30 I. The substance is heated to boiling with 75 ml of alcohol and the product is filtered off while warm. Yield 6.1 g (89%), melting point 191°, $[\alpha]_D^{22} = -6.3°$ (c=1, dimethylformamide).

(K) H-Arg-Lys-Glu-Val-Tyr-O-n-butyl acetate 5.74 g (4.2 mmoles) of Z-Arg(Z₂)-Lys(Boc)-Glu(OBu$^t$)-Val-Tyr(Bu$^t$)-O-n-butyl are treated with 90 percent trifluoroacetic acid analogously to Example 30 K. Yield 4.99 g. 4.9 g of the substance obtained above are subjected to catalytic hydrogenation and the product is worked up analogously to Example 30 L. Yield 3.151 g. 800 mg of the substance are purified further by being chromatographed on a hydroxypropylated, crosslinked dextran gel in 90 percent strength methanol. Yield 604 mg. $[\alpha]_D^{23} = -46.6°$ (c=1, water).

EXAMPLE 34

Arg-Lys-Glu-Val-Tyr-O-CH(CH₃)₂ acetate

(A) H-Tyr(Buᵗ)-O-CH(CH₃)₂.HCl 18.6 g (50 mmoles) of Z-Tyr(Bu$^t$)-OH in 30 ml of pyridine are reacted with 30 ml of isopropanol and 40 ml of a 50 percent solution of propylphosphonic anhydride in methylene chloride analogously to Example 30 A. The resulting oil is subjected to catalytic hydrogenation analogously to Example 25 B. The substance crystallizes from ether. Yield 13.15 g (83%), melting point 161°–163°, $[\alpha]_D^{23} = +15.7°$ (c=1, methanol).

(B) Z-Val-Tyr(Buᵗ)-O-CH(CH₃)₂

7.9 g (25 mmoles) of H-Tyr(Bu$^t$)-O-CH(CH₃)₂ hydrochloride and 6.27 g (25 mmoles) of Z-Val-OH are subjected to a condensation reaction analogously to Example 30 C. Yield 11.8 g (92%), melting point 133°–134°, $[\alpha]_D^{26} = -25.2°$ (c=1, methanol).

(C) H-Val-Tyr(Buᵗ)-O-CH(CH₃)₂.HCl 11.26 g (22 mmoles) of Z-Val-Tyr(Bu$^t$)-O-CH(CH₃)₂ are subjected to catalytic hydrogenation analogously to Example 30 D. Yield 8.88 g (97%), melting point 126°, with decomposition, $[\alpha]_D^{25} = +20.8°$ (c=1, methanol).

(D) Z-Glu(OBuᵗ)-Val-Tyr(Buᵗ)-O-CH(CH₃)₂

8.3 g (20 mmoles) of H-Val-Tyr(Bu$^t$)-O-CH(CH₃)₂.HCl are reacted with 10.83 g (21 mmoles) of Z-Glu(OBu$^t$)-OTcp analogously to Example 30 E. Yield 7.42 g (53%), melting point 159°, $[\alpha]_D^{25} = -27.6°$ (c=1, methanol).

(E) H-Glu(OBuᵗ)-Val-Tyr(Buᵗ)-O-CH(CH₃)₂.HCl 6.96 g (10 mmoles) of Z-Glu(OBu$^t$)-Val-Tyr(Bu$^t$)-O-CH(CH₃)₂ are subjected to catalytic hydrogenation analogously to Example 30 F. The residue is dried at a high temperature. It is soluble in ether. Yield 5.82 g (97%), melting point 133°, $[\alpha]_D^{23} = +6.5°$ (c=1, methanol).

(F) Z-Lys(Boc)-Glu(OBuᵗ)-Val-Tyr(Buᵗ)-O-CH(CH₃)₂

5.68 g (9.5 mmoles) of H-Glu(OBu$^t$)-Val-Tyr(Bu$^t$)-O-CH(CH₃)₂.HCl are reacted with 5.87 g (10.5 mmoles) of Z-Lys(Boc)-OTcp analogously to Example 30 G. Yield 8.0 g (91%), melting point 149°, $[\alpha]_D^{22} = -30.2°$ (c=1, methanol).

(G) H-Lys(Boc)-Glu(OBuᵗ)-Val-Tyr(Buᵗ)-O-CH(CH₃)₂.HCl 7.4 g (8 mmoles) of Z-Lys(Boc)-Glu(OBu$^t$)-Val-Tyr(Bu$^t$)-O-n-butyl are subjected to catalytic hydrogenation analogously to Example 30 H. The residue is triturated with ether. Yield 6.3 g (95%), melting point 179°–180°, with decomposition, $[\alpha]_D^{22} = -16.4°$ (c=1, methanol).

(H) Z-Arg(Z₂)-Lys(Boc)-Glu(OBuᵗ)-Val-Tyr(Buᵗ)-O-CH(CH₃)₂

5.79 g (7 mmoles) of H-Lys(Boc)-Glu(OBu$^t$)-Val-Tyr(Bu$^t$)-O-CH(CH₃)₂.HCl are reacted with 5.67 g of Z-Arg(Z₂)-OTcp analogously to Example 30 I. The substance is heated to boiling with 100 ml of alcohol and the product is filtered off while warm. Yield 7.23 g (76.5%), melting point 188°, $[\alpha]_D^{22} = -7.3°$ (c=1, in dimethylformamide).

(I) H-Arg-Lys-Glu-Val-Tyr-O-CH(CH₃)₂ acetate 6.75 g (5 mmoles) of Z-Arg(Z₂)-Lys(Boc)-Glu(OBu$^t$)-Val-Tyr(Bu$^t$)-O-CH(CH₃)₂ are treated with 90 percent trifluoroacetic acid analogously to Example 30 K. Yield 5.66 g.

5.6 g of the substance obtained above are subjected to catalytic hydrogenation and the product is worked up analogously to Example 30 L. Yield 3.449 g. 800 mg of the substance are purified further by being chromatographed on a hydroxypropylated, crosslinked dextran gel in 90 percent strength methanol. Yield 642 mg, $[\alpha]_D^{23} = -42.0°$ (c=1, water).

EXAMPLE 35

Arg-Lys-Glu-Val-Tyr-NH-C₂H₅ acetate

(A) Z-Tyr(Buᵗ)-NH-C₂H₅

3.2 ml (25 mmoles) of N-ethylmorpholine and 5.56 g (27 mmoles) of dicyclohexylcarbodiimide are added at 0° C. to a solution in 50 ml of dimethylformamide of 9.27 g (25 mmoles) of Z-Tyr(Bu$^t$)-OH, 2.03 g (25 mmoles) of ethylamine hydrochloride and 3.38 g of 1-hydroxybenzotriazole. The mixture is stirred for two hours at 0° C. and for 5 hours at room temperature and is left to stand overnight at room temperature. The precipitate is filtered off and the filtrate is concentrated. The resulting oil is partitioned between ethyl acetate and water. The ethyl acetate phase is extracted by shaking with KHSO₄ solution, NaHCO₃ solution and water, is dried over Na₂SO₄ and is concentrated. The residue cyrstallizes from petroleum ether. Yield 9.63 g (96% ), melting point 107°–110°, $[\alpha]_D^{22} = -0.5°$ (c=1, methanol).

(B) H-Tyr(Buᵗ)-NH-C₂H₅.HCl 9.5 g (23.8 mmoles) of Z-Tyr(Bu$^t$)-NH-C₂H₅ are subjected to catalytic hydrogenation analogously to Example 25 B. The substance crystallizes from ether. Yield 6.9 g (96%), melting point 163°, with decomposition, $[\alpha]_D^{24} = +45.2°$ (c=1, in methanol).

(C) Z-Val-Tyr(Bu$^t$)-NH-C$_2$H$_5$ 6.27 g (25 mmoles) of Z-Val-OH and 7.52 g (25 mmoles) of H-Tyr(Bu$^t$)-NH-C$_2$H$_5$.HCl are subjected to a condensation reaction analogously to Example 30 C. After being precipitated by means of water, the substance is dissolved in 70 ml of 95 percent strength alcohol and the solution is filtered hot and cooled (3 hours at 4° C.). The precipitate is filtered off. Yield 9.01 g (72.5%), melting point 181°, $[\alpha]_D^{23} = -39.8°$ (c=1, dimethylformamide).

(D) H-Val-Tyr(Bu$^t$)-NH-C$_2$H$_5$.HCl 8.7 g (17.5 mmoles) of Z-Val-Tyr(Bu$^t$)-NH-C$_2$H$_5$ are subjected to catalytic hydrogenation in 125 ml of methanol and 50 ml of dimethylformamide analogously to Example 25 B. The substance crystallizes from ether. Yield 6.52 g (93%), melting point 203°–205°, with decomposition, $[\alpha]_D^{23} = +28.0°$ (c=1, methanol).

(E) Z-Glu(OBu$^t$)-Val-Tyr(Bu$^t$)-NH-C$_2$H$_5$ 6.18 g (15.5 mmoles) of H-Val-Tyr(Bu$^t$)-NH-C$_2$H$_5$.HCl are reacted with 8.25 g (16 mmoles) of Z-Glu(OBu$^t$)-OTcp analogously to Example 30 E. After precipitation by means of water, the substance is dissolved in 120 ml of hot 95 percent strength alcohol and the solution is filtered while hot. The filtrate is allowed to stand overnight at 4° C. and the precipitate is filtered off. Yield 8.12 g (76%), melting point 209°, $[\alpha]_D^{24} = -24.4°$ (c=1, dimethylformamide).

(F) H-Glu(OBu$^t$)-Val-Tyr(Bu$^t$)-NH-C$_2$H$_5$.HCl 7.51 g (11 mmoles) of Z-Glu(OBu$^t$)-Val-Tyr(Bu$^t$)-NH-C$_2$H$_5$ are subjected to catalytic hydrogenation analogously to Example 35 D. The substance crystallizes from ether. Yield 6.35 g (98%), melting point 199°–200°, with decomposition, $[\alpha]_D^{23} = -6.7°$ (c=1, methanol).

(G) Z-Lys(Boc)-Glu(OBu$^t$)-Val-Tyr(Bu$^t$)-NH-C$_2$H$_5$ 5.85 g (10 mmoles) of H-Glu(OBu$^t$)-Val-Tyr(Bu$^t$)-NH-C$_2$H$_5$.HCl are reacted with 5.87 g (10.5 mmoles) of Z-Lys(Boc)-OTcp analogously to Example 30 G. After being precipitated by means of water, the substance is recrystallized from 100 ml of 95 percent strength alcohol. Insoluble matter is filtered off from the hot solution. The solution is allowed to stand overnight at 4° C. and the precipitate is then filtered off. Yield 6.37 g (67%), melting point 216°–217°, $[\alpha]_D^{22} = -26.8°$ (c=1, in dimethylformamide).

(H) H-Lys(Boc)-Glu(OBu$^t$)-Val-Tyr(Bu$^t$)-NH-C$_2$H$_5$.HCl 6 g (6.66 mmoles) of Z-Lys(Boc)-Glu(OBu$^t$)-Val-Tyr(Bu$^t$)-NH-C$_2$H$_5$ are subjected to catalytic hydrogenation analogously to Example 25 B. The substance crystallizes from ether. Yield 4.77 g (89%), melting point 240°–242°, with decomposition, $[\alpha]_D^{26} = -24.9°$ (c=1, methanol).

(I) Z-Arg(Z$_2$)-Lys(Boc)-Glu(OBu$^t$)-Val-Tyr(Bu$^t$)-NH-C$_2$H$_5$ 4.07 g (5 mmoles) of H-Lys(Boc)-Glu(OBu$^t$)-Val-Tyr(Bu$^t$)-NH-C$_2$H$_5$.HCl are reacted with 3.97 g (5.25 mmoles) of Z-Arg(Z$_2$)-OTcp analogously to Example 30 I. After being precipitated by means of water, the substance is dried and triturated with ether. Yield 6.66 g (99.8%), melting point 222°–224°, with decomposition, $[\alpha]_D^{25} = -18.1°$ (c=1, acetic acid).

(K) H-Arg-Lys-Glu-Val-Tyr-NH-C$_2$H$_5$ acetate 6.0 g (4.5 mmoles) of Z-Arg(Z$_2$)-Lys(Boc)-Glu(OBu$^t$)-Val-Tyr(Bu$^t$)-NH-C$_2$H$_5$ are treated with 90 percent strength trifluoroacetic acid analogously to Example 30 K. Yield 4.85 g.

4.8 g of the substance obtained above are subjected to catalytic hydrogenation and the product is worked up analogously to Example 30 L. Yield 3.15 g. 800 mg of the substance are purified further by being chromatographed on a hydroxypropylated, crosslinked dextran gel in 70 percent strength methanol. Yield 465 mg, $[\alpha]_D^{24} = -47.1°$ (c=1, water). Aminoacid analysis: Glu (0.98), Val (1.00), Tyr (0.85), Lys (1.01) and Arg (1.00), content of peptide base: approx. 80%.

EXAMPLE 36

Arg-Lys-Glu-Val-Tyr-NH-CH$_2$-CH(CH$_3$)$_2$ acetate

(A) Z-Tyr-NH-CH$_2$-CH(CH$_3$)$_2$ 18.6 g (50 mmoles) of Z-Tyr(Bu$^t$)-OH are subjected to a condensation reaction with 5 ml (50 mmoles) of isobutylamine analogously to Example 35 A. Yield 17.19 g (80%), melting point 114°–115°, $[\alpha]_D^{23} = -3.0°$ (c=1, methanol).

(B) H-Tyr-NH-CH$_2$-CH(CH$_3$)$_2$.HCl 17 g (approx. 40 mmoles) of Z-Tyr-NH-CH$_2$-CH(CH$_3$)$_2$ are subjected to catalytic hydrogenation analogously to Example 25 B. Yield 13.2 g (100%), melting point 172°, $[\alpha]_D^{23} = +45.7°$ (c=1, methanol).

(C) Z-Val-Tyr-NH-CH$_2$-CH(CH$_3$)$_2$ 8.22 g (25 mmoles) of H-Tyr-NH-CH$_2$-CH(CH$_3$)$_2$ hydrochloride and 6.27 g (25 mmoles) of Z-Val-OH are subjected to a condensation reaction analogously to Example 35 C. Yield 10.51 g (79%), melting point 207°, $[\alpha]_D^{23} = -37.8°$ (c=1, dimethylformamide).

(D) H-Val-Tyr-NH-CH$_2$-CH(CH$_3$)$_2$.HCl 9.95 g (19 mmoles) of Z-Val-Tyr(Bu$^t$)-NH-CH$_2$-CH(CH$_3$)$_2$ are subjected to catalytic hydrogenation analogously to Example 35 D. Yield 8.13 g (100%), melting point 201°–203°, $[\alpha]_D^{23} = +24.6°$ (c=1, methanol).

(E) Z-Glu(OBu$^t$)-Val-Tyr(Bu$^t$)-NH-CH$_2$-CH(CH$_3$)$_2$ 7.7 g (18 mmoles) of H-Val-Tyr(Bu$^t$)-NH-CH$_2$-CH(CH$_3$)$_2$.HCl are reacted with 9.83 g (19 mmoles) of Z-Glu(OBu$^t$)-OTcp analogously to Example 35 E. Yield 8.37 g (65%), melting point 173°–174°, $[\alpha]_D^{22} = -23.8°$ (c=1, dimethylformamide).

(F) H-Glu(OBu$^t$)-Val-Tyr(Bu$^t$)-NH-CH$_2$-CH(CH$_3$)$_2$.HCl 7.82 g (11 mmoles) of Z-Glu(OBu$^t$)-Val-Tyr(Bu$^t$)-NH-CH$_2$-CH(CH$_3$)$_2$ are subjected to catalytic hydrogenation analogously to Example 35 D. The substance is soluble to some extent in ether and it is therefore not triturated with ether. Yield 6.16 g (91%), melting point 202°–205°, with decomposition, $[\alpha]_D^{26} = -10.4°$ (c=1, methanol).

(G) Z-Lys(Boc)-Glu(OBu$^t$)-Val-Tyr(Bu$^t$)-NH-CH$_2$-CH(CH$_3$)$_2$ 5.82 g (9.5 mmoles) of H-Glu(OBu$^t$)-Val-Tyr(Bu$^t$)-NH-CH$_2$-CH(CH$_3$)$_2$.HCl are reacted with 5.6 g (10 mmoles) of Z-Lys(Boc)-OTcp analogously to Example 30 G. The substance is purified by being boiled with 100 ml of ethyl acetate. 100 ml of petroleum ether are added to the resulting solution and the precipitate is filtered off. Yield 7.9 g (88%), melting point 209°–211° C., $[\alpha]_D^{24} = -34.9°$ (c=1, methanol).

(H) H-Lys(Boc)-Glu(OBu$^t$)-Val-Tyr(Bu$^t$)-NH-CH$_2$-CH(CH$_3$)$_2$.HCl 7.5 g (8 mmoles) of Z-Lys(Boc)-Glu(OBu$^t$)-Val-Tyr(Bu$^t$)-NH-CH$_2$-CH(CH$_3$)$_2$ are subjected to catalytic hydrogenation analogously to Example 25 B. The substance crystallizes from ether. Yield 6.0 g (89%), melting point 244°–245°, $[\alpha]_D^{24} = -25.9°$ (c=1, methanol).

(I) Z-Arg(Z$_2$)-Lys(Boc)-Glu(OBu$^t$)-Val-Tyr(Bu$^t$)-NH-CH$_2$-CH(CH$_3$)$_2$ 5.46 g (6.5 mmoles) of H-Lys(Boc)-Glu(OBu$^t$)-Val-Tyr(Bu$^t$)-NH-CH$_2$-CH(CH$_3$)$_2$.HCl are reacted with 4.91 g (6.5 mmoles) of Z-Arg(Z$_2$)-OTcp analogously to Example 30 I. The substrate is extracted by boiling with 150 ml of ethyl acetate and the precipitate is filtered off after adding 150 ml of petroleum ether. Yield 8.79 g (99%), melting point 214°–216°, $[\alpha]_D^{24} = -18.4°$ (c=1, glacial acetic acid).

(K) H-Arg-Lys-Glu-Val-Tyr-NH-CH$_2$-CH(CH$_3$)$_2$ acetate 8.18 g (6 mmoles) of Z-Arg(Z$_2$)-Lys(Boc)-Glu(OBu$^t$)-Val-Tyr(Bu$^t$)-NH-CH$_2$-CH(CH$_3$)$_2$ are treated with 90 percent strength trifluoroacetic acid analogously to Example 30 K. Yield 8.6 g (still containing water and trifluoroacetic acid).

8 g of the substance obtained above are subjected to catalytic hydrogenation and the product is worked up analogously to Example 30 L. Yield 3.98 g. 800 mg of the substance are purified further by being chromatographed on a hydroxypropylated, crosslinked dextran gel in 70 percent strength methanol. Yield 650 mg, $[\alpha]_D^{22} = -52.7°$ (c=1, methanol).

EXAMPLE 37

Arg-Lys-Glu-Val-Tyr-piperidide

(A) Z-Tyr(Bu$^t$)-piperidide 9.27 g (25 mmoles) of Z-Tyr(Bu$^t$)-OH and 2.48 ml (25 mmoles) of piperidine are subjected to a condensation reaction analogously to Example 35 A. Yield 10.1 g (92%) of a nearly colorless oil.

(B) H-Tyr(Bu$^t$)-piperidide.HCl 10.1 g (23 mmoles) of Z-Tyr(Bu$^t$)-piperidide are subjected to catalytic hydrogenation analogously to Example 25 B. The substance crystallizes from ether. Yield 7.51 g (95%), melting point 205°, $[\alpha]_D^{23} = +47.1°$ (c=1, methanol).

(C) Z-Val-Tyr(Bu$^t$)-piperidide 8.52 g (25 mmoles) of H-Tyr(Bu$^t$)-piperidide.HCl and 6.27 g (25 mmoles) of Z-Val-OH are subjected to a condensation reaction analogously to Example 35 C. The substance crystallizes from ether. Yield 7.97 g (70%), melting point 142° C., $[\alpha]_D^{23} = -32.8°$ (c=1, methanol).

(D) H-Val-Tyr(Bu$^t$)-piperidide.HCl 7.47 g (16.5 mmoles) of Z-Val-Tyr(Bu$^t$)-piperidide are subjected to catalytic hydrogenation analogously to Example 25 B. The substance is dried at high temperature. It does not crystallize from ether. Yield 5.92 g of an amorphous substance which decomposes at about 174° C., $[\alpha]_D^{23} = +25.2°$ (c=1, methanol).

(E) Z-Glu(OBu$^t$)-Val-Tyr(Bu$^t$)-piperidide 5.5 g (12.5 mmoles) of H-Val-Tyr(Bu$^t$)-piperidide.HCl are reacted with 6.71 g (13 mmoles) of Z-Glu(OBu$^t$)-OTcp analogously to Example 30 E. The substance is oily and is shaken with ethyl acetate. It is purified by being chromatographed in methylene chloride on 250 g of silica gel. Trichlorophenol is eluted with methylene chloride. The peptide is eluted with a mixture of methylene chloride and acetone, such as 8:2. Yield 7.3 g (80%), $[\alpha]_D^{24} = -41.4°$ (c=1, methanol), melting point 90°–98° (amorphous).

(F) H-Glu(OBu$^t$)-Val-Tyr(Bu$^t$)-piperidide.HCl 6.5 g (9 mmoles) of Z-Glu(OBu$^t$)-Val-Tyr(Bu$^t$)-piperidide are subjected to catalytic hydrogenation analogously to Example 25 B. The substance is triturated with ether. Yield 5.16 g (92%) of an amorphous substance, $[\alpha]_D^{23} = -18.9°$ (c=1, methanol).

(G) Z-Lys(Boc)-Glu(OBu$^t$)-Val-Tyr(Bu$^t$)-piperidide 4.96 g (8 mmoles) of H-Glu(OBu$^t$)-Val-Tyr(Bu$^t$)-piperidide.HCl are reacted with 4.76 g (8.5 mmoles) of Z-Lys(Boc)-OTcp analogously to Example 30 G. The substance crystallizes from diisopropyl ether/petroleum ether. Yield 6.5 g (85%), melting point 160°–161° C., $[\alpha]_D^{23} = -40.1°$ (c=1, methanol).

(H) H-Lys(Boc)-Glu(OBu$^t$)-Val-Tyr(Bu$^t$)-piperidide.HCl 6.0 g (6.3 mmoles) of Z-Lys(Boc)-Glu(OBu$^t$)-Val-Tyr(Bu$^t$)-piperidide are subjected to catalytic hydrogenation analogously to Example 25 B. The substance is triturated with ether and filtered off. Yield 4.48 g (83%), melting point 171°–174°, with decomposition, $[\alpha]_D^{23} = -28.0°$ (c=1, methanol).

(I) Z-Arg(Z$_2$)-Lys(Boc)-Glu(OBu$^t$)-Val-Tyr(Bu$^t$)-piperidide 4.26 g (5 mmoles) of H-Lys(Boc)-Glu(OBu$^t$)-Val-Tyr(Bu$^t$)-piperidide.HCl are reacted with 3.97 g (5.25 mmoles) of Z-Arg(Z$_2$)-OTcp analogously to Example 30 I. The substance is triturated with ether. Yield 6.06 g (88%), melting point 177°–178°, $[\alpha]_D^{23} = -11.2°$ (c=1, dimethylformamide).

(K) H-Arg-Lys-Glu-Val-Tyr-piperidide acetate 5.5 g (4 mmoles) of Z-Arg(Z$_2$)-Lys(Boc)-Glu(OBu$^t$)-Val-Tyr(Bu$^t$)-piperidide are treated with 90 percent strength trifluoroacetic acid analogously to Example 30 K. Yield 4.83 g.

4.55 g of the substance obtained above are subjected to catalytic hydrogenation and the product is worked up analogously to Example 30 L. Yield 2.6 g. 800 mg of the substance are purified further by being chromatographed on a hydroxypropylated, crosslinked dextran gel in 90 percent strength methanol. Yield 613 mg, $[\alpha]_D^{27} = -45.4°$ (c=1, water).

EXAMPLE 38

Arg-Lys-D-Aad-Val-Tyr-OMe acetate (A) Z-D-Aad(OBu$^t$)-Val-Tyr(Bu$^t$)-OMe 1.28 ml (10 mmoles) of N-ethylmorpholine and 2.1 g of dicyclohexylcarbodiimide are added at 0° C. to a solution in 20 ml of dimethylformamide of 3.54 g (10 mmoles) of Z-D-Aad(OBu$^t$)-OH, 3.86 g (10 mmoles) of H-Val-Tyr(Bu$^t$)-OMe.HCl and 1.35 g (10 mmoles) of 1-hydroxybenzotriazole. The mixture is stirred for 1 hour at 0° C. and then at room temperature. It is left to stand overnight and the precipitate is filtered off on the following day. The filtrate is concentrated in a high vacuum and the residue is partitioned between ethyl acetate and water. The ethyl acetate phase is extracted by shaking successively with saturated NaHCO$_3$ solution, KHSO$_4$ solution and water, is dried over Na$_2$SO$_4$ and is concentrated. The residue crystallizes from petroleum ether. Yield 5.96 g. The substance is purified further by hot recrystallization from 90 ml of isopropyl ether and 30 ml of isopropanol. Yield 2.48 g, melting point 104°-107°, $[\alpha]_D^{23} = -11.5°$ (c=1, methanol).

(B) H-D-Aad(OBu$^t$)-Val-Tyr(Bu$^t$)-OMe.HCl

Pd-on-charcoal catalyst is added to a solution of 2.3 g of Z-D-Aad(OBu$^t$)-Val-Tyr(Bu$^t$)-OMe in 100 ml of methanol and hydrogen is passed through the solution at pH 4.5 (autotitrator), while stirring and while adding approx. 2 N methanolic hydrochloric acid, until no further methanolic hydrochloric acid is taken up. The catalyst is then filtered off and the filtrate is concentrated. Yield 1.98 g, melting point 85°-87°, $[\alpha]_D^{22} = -14.9°$ (c=1, methanol).

(C) Z-Lys(Boc)-D-Aad(OBu$^t$)-Val-Tyr(Bu$^t$)-OMe 0.41 ml of N-ethylmorpholine and 2 g of Z-Lys(Boc)-OTcp are added at 0° C. to a solution of 1.91 g of H-D-Aad(OBu$^t$)-Val-Tyr(Bu$^t$)-OMe.HCl and 0.44 g of 1-hydroxybenzotriazole in 10 ml of dimethylformamide. The solution is allowed to stand for one hour at 0° C. and for 3 hours at room temperature and is then concentrated in a high vacuum and worked up as under A. The substance crystallizes from petroleum ether. Yield 2.65 g, melting point 165°, $[\alpha]_D^{22} = -3.5°$ (c=1, methanol).

(D) H-Lys(Boc)-D-Aad(OBu$^t$)-Val-Tyr(Bu$^t$)-OMe.HCl 2.3 g of Z-Lys(Boc)-D-Aad(OBu$^t$)-Val-Tyr(Bu$^t$)-OMe are subjected to catalytic hydrogenation analogously to B. The residue is triturated with petroleum ether. Yield 1.38 g, melting point 115°-117°, $[\alpha]_D^{22} = +3.2°$ (c=1, methanol).

(E) Z-Arg(Z$_2$)-Lys(Boc)-D-Aad(OBu$^t$)-Val-Tyr(Bu$^t$)-OMe 0.19 ml of N-ethylmorpholine and 1.12 g of Z-Arg(Z$_2$)-OTcp are added at 0° C. to a solution of 1.2 g of H-Lys(Boc)-D-Aad(OBu$^t$)-Val-Tyr(Bu$^t$)-OMe.HCl and 0.2 g of 1-hydroxybenzotriazole in 10 ml of dimethylformamide. The mixture is stirred for 1 hour at 0° C. and for 4 hours at room temperature. 100 ml of ice water, to which about 5 ml of saturated NaHCO$_3$ solution have been added, are used to produce a precipitate, which is washed thoroughly with KHSO$_4$ solution and water. The substance is dried over P$_2$O$_5$ and triturated with 30 ml of ether. The substance is filtered off and dried. Yield 1.74 g, melting point 167°-170°, $[\alpha]_D^{22} = -3.1°$ (c=1, 90 percent strength acetic acid).

(F) H-Arg-Lys(Boc)-D-Aad(OBu$^t$)-Val-Tyr(Bu$^t$)-OMe.2HCl 1.5 g of Z-Arg(Z$_2$)-Lys(Boc)-D-Aad(OBu$^t$)-Val-Tyr(Bu$^t$)-OMe are subjected to catalytic hydrogenation analogously to B. The residue is triturated with ether and filtered off. Yield 1.05 g, melting point 112°-114°, $[\alpha]_D^{22} = +8.7°$ (c=1, 90 percent strength acetic acid).

(G) H-Arg-Lys-D-Aad-Val-Tyr-OMe acetate 1 g of H-Arg-Lys(Boc)-D-Aad(OBu$^t$)-Val-Tyr(Bu$^t$)-OMe.2HCl is dissolved in 10 ml of 90 percent strength trifluoroacetic acid. The mixture is allowed to stand for one hour at room temperature and is concentrated in vacuo and the residue is distilled with methanol. The residue is dissolved in water and chromatographed over a basic ion exchanger in the acetate form. The eluate is freeze-dried and then chromatographed in 90 percent strength methanol on a hydroxypropylated, crosslinked dextran gel. Yield 340 mg, aminoacid analysis (hydrolysis: 24 hours at 120° C.): Aad (0.81), Val (0.94), Tyr (0.84), Lys (1.00) and Arg (1.00), content of peptide base: approx. 80%.

EXAMPLE 39

Arg-Lys-D-Asp-Val-Tyr-OMe acetate (A) Z-D-Asp(OBu$^t$)-Val-Tyr(Bu$^t$)-OMe 6.46 g (20 mmoles) of Z-D-Asp(OBu$^t$)-OH are subjected to a condensation reaction with 7.73 g (20 mmoles) of H-Val-Tyr(Bu$^t$)-OMe.HCl in 50 ml of dimethylformamide analogously to Examples 38 A. Yield 11.2 g (85%), melting point 90°-92°, $[\alpha]_D^{27} = -3.5°$ (c=1, methanol).

(B) H-D-Asp(OBu$^t$)-Val-Tyr(Bu$^t$)-OMe.HCl 10.49 g (16 mmoles) of Z-D-Asp(OBu$^t$)-Val-Tyr(Bu$^t$)-OMe are subjected to catalytic hydrogenation analogously to Example 38 B. The residue is dissolved in ether. An insoluble residue is filtered off and the filtrate is concentrated and dried in a high vacuum. Yield 8.79 g (98%), amorphous, $[\alpha]_D^{27} = -10.4°$ (c=1, methanol).

(C) Z-Lys(Boc)-D-Asp(OBu$^t$)-Val-Tyr(Bu$^t$)-OMe 8.37 g (15 mmoles) of H-D-Asp(OBu$^t$)-Val-Tyr(Bu$^t$)-OMe.HCl are reacted with 8.68 g (15.5 mmoles) of Z-Lys(Boc)-OTcp analogously to Example 38 C. The substance crystallizes from petroleum ether. Yield 11.52 g (87%), melting point 142°-145°, $[\alpha]_D^{27} = +3.4°$ (c=1, methanol).

(D) H-Lys(Boc)-D-Asp(OBu$^t$)-Val-Tyr(Bu$^t$)-OMe.HCl 11.05 g (12.5 mmoles) of Z-Lys(Boc)-D-Asp(OBu$^t$)-Val-Tyr(Bu$^t$)-OMe are subjected to catalytic hydrogenation analogously to Example 38 B. Yield 9.1 g (92%), amorphous, $[\alpha]_D^{27} = +17.6°$ (c=1, methanol).

(E) Z-Arg(Z$_2$)-Lys(Boc)-D-Asp(OBu$^t$)-Val-Tyr(Bu$^t$)-OMe 1.57 g (2 mmoles) of H-Lys(Boc)-D-Asp(OBu$^t$)-Val-Tyr(Bu$^t$)-OMe.HCl are reacted with 1.6 g (2.2 mmoles) of Z-Arg(Z$_2$)-OTcp analogously to Example 38 E and the product is worked up analogously to Example 38 A. the substance is purified by being chromatographed over 80 g of silica gel. The eluting agent is a methylene chloride/acetone mixture, in proportions such as 7:3. The residue is triturated with petroleum ether. Yield 1.97 g (75%), melting point 150°–154°, $[\alpha]_D^{25} = +7.2°$ (c=1, dimethylformamide).

(F) H-Arg-Lys-D-Asp-Val-Tyr-OMe acetate 1.3 g (1 mmole) of Z-Arg(Z$_2$)-Lys(Boc)-D-Asp(OBu$^t$)-Val-Tyr(Bu$^t$)-OMe are dissolved in 5 ml of 90 percent strength trifluoroacetic acid. The mixture is allowed to stand for one hour at room temperature and is concentrated in vacuo. The residue is triturated with water, filtered off and dried. The substance, which still contains a little water and trifluoroacetic acid, is dissolved in 10–20 ml of 90 percent strength acetic acid. Pd-on-charcoal catalyst is added to this solution and hydrogen is passed through the solution until $CO_2$ is no longer evolved. The catalyst is filtered off, the filtrate is concentrated and the residue is dissolved in water. The solution is chromatographed on a weakly basic ion exchanger in the acetate form (30×2 cm). The product is eluted with water. The peptide-containing eluate is freeze-dried and purified further by being chromatographed on a hydroxypropylated, crosslinked dextran gel in 90 percent strength methanol. Yield 430 mg, aminoacid analysis: Asp (1.00), Val (1.1), Tyr (0.9), Lys (1.09) and Arg (0.98), content of peptide base: approx. 78%.

EXAMPLE 40

Arg-Lys-D-Glu-Val-Tyr-OMe acetate (A) Z-D-Glu(OBu$^t$)-Val-Tyr(Bu$^t$)-OMe 4.04 g (12 mmoles) of Z-D-Glu(OBu$^t$)-OH are subjected to a condensation reaction with 4.64 g (12 mmoles) of H-Val-Tyr(Bu$^t$)-OMe.HCl in 25 ml of dimethylformamide analogously to Example 38 A. Yield 6.72 g. The substance is purified further by chromatography on silica gel. The eluting agent is a mixture of methylene chloride and acetone in proportions such as 9:1. Yield 6.63 g (70%), melting point 100°–104°, $[\alpha]_D^{27} = -8.4°$ (c=1, methanol).

(B) H-D-Glu(OBu$^t$)-Val-Tyr(Bu$^t$)-OMe.HCl 5.4 g (8 mmoles) of Z-D-Glu(OBu$^t$)-Val-Tyr(Bu$^t$)-OMe are subjected to catalytic hydrogenation analogously to Example 38 B. The residue is dried in a high vacuum. Yield 4.57 g (100%). The substance is amorphous.

(C) Z-Lys(Boc)-D-Glu(OBu$^t$)-Val-Tyr(Bu$^t$)-OMe 4.57 g (8 mmoles) of H-D-Glu(OBu$^t$)-Val-Tyr(Bu$^t$)-OMe.HCl are reacted with 4.76 g (8.5 mmoles) of Z-Lys(Boc)-OTcp analogously to Example 38 C. The substance is precipitated from the dimethylformamide solution by means of 250 ml of water to which 10 ml of saturated NaHCO$_3$ solution are added. The precipitate is filtered off and washed thoroughly with water and dried. The substance is then triturated with diethyl ether, filtered off and dried. Yield 6.22 g (87%), melting point 164°–167°, $[\alpha]_D^{25} = -1°$ (c=1, dimethylformamide).

(D) H-Lys(Boc)-D-Glu(OBu$^t$)-Val-Tyr(Bu$^t$)-OMe.HCl 6.01 g (6.6 mmoles) of Z-Lys(Boc)-D-Glu(OBu$^t$)-Val-Tyr(Bu$^t$)-OMe are subjected to catalytic hydrogenation analogously to Example 38 B. Yield 5.28 g (100%), $[\alpha]_D^{24} = +8.6°$ (c=1, methanol).

(E) Z-Arg(Z$_2$)-Lys(Boc)-D-Glu(OBu$^t$)-Val-Tyr(Bu$^t$)-OMe 1.6 g (2 mmoles) of H-Lys(Boc)-D-Glu(OBu$^t$)-Val-Tyr(Bu$^t$)-OMe.HCl are reacted with 1.66 g (2.2 mmoles) of Z-Arg(Z$_2$)-OTcp analogously to Example 38 E. The product is worked up analogously to Example 40 C. Yield 2.44 g (94%), melting point 153°–156°, $[\alpha]_D^{25} = 0$ (c=1, dimethylformamide).

(F) H-Arg-Lys-D-Glu-Val-Tyr-OMe acetate 1.32 g (1 mmole) of Z-Arg(Z$_2$)-Lys(Boc)-D-Glu(OBu$^t$)-Val-Tyr(Bu$^t$)-OMe are reacted analogously to Example 39 F. Yield 445 mg. Aminoacid analysis: Glu (1.00), Val (0.96), Tyr (0.91), Lys (1.04) and Arg (0.95), content of peptide base: approx. 80%.

We claim:

1. A peptide of the formula

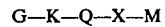

wherein
G is arginine, lysine, ornithine, or homoarginine, all in the L- or their D-configuration, or is unsubstituted ω-aminoalkanoyl, ω-guanidinoalkanoyl, or ω-dimethylaminoalkanoyl having 3–6 C atoms, or is such ω-aminoalkanoyl, ω-guanidinoalkanoyl, or ω-dimethylaminoalkanoyl substituted with an d amino group in the L- or D-configuration, which amino group in turn may carry
alkanoyl having 1–6 C atoms,
aroyl having 7–11 C atoms,
cycloalkanoyl having up to 2 alkyl C atoms and 5–7 cycloalkyl C atoms,
aralkanoyl having up to a total of 9 C atoms and wherein a —CH$_2$— group can be replaced by —O— or —S—, alkoxycarbonyl or aralkyloxycarbonyl having up to 7 carbon atoms, or
succinoyl, succinamoyl, glutaroyl, glutaminyl, pyroglutamyl, phthaloyl, phthalamidyl, or 2-carboxybenzoyl;
K is a basic amino acid;
Q is L- or D-glutamic acid, D-aspartic acid, or D-α-aminoadipic acid;
X is L-valine or L-isoleucine; and
M is an L- or D-aminoacid having a hydrophobic side chain,
or is an ester, amide, alkylamide, or alkylester having 1–6 C atoms of such an acid, or is an aralkylester having 7–10 C atoms of such an acid.

2. A peptide as in claim 1 wherein K is L-lysine, L-arginine, L-homoarginine, or L-ornithine.

3. The method of influencing the maturing of thymus-dependent lymphocytes which comprises treating said lymphocytes with a peptide as in claim 1.

4. A peptide as in claim 1 which is Arg-Lys-Glu-Val-Tyr-OMe.

5. A peptide as in claim 1 which is D-Lys-Arg-Glu-Val-Tyr-OMe.

6. A peptide as in claim 1 which is Arg-Lys-D-Aad-Val-Tyr-OMe.

7. A peptide as in claim 1 which is Arg-Lys-D-Glu-Val-Tyr-OMe.

8. A peptide as in claim 1 which is Arg-Lys-Glu-Val-Trp-OMe.

9. A peptide as in claim 1 wherein K is L-lysine, L-arginine, L-homoarginine, or L-ornithine and M is an amino acid selected from the group consisting of Ala, Val, Leu, Ile, Met, Phe, Pro, Tyr, Phg (C-phenylglycine), Ser(Bu$^t$), Thr(Bu$^t$), Cys(Bu$^t$), Cys(Et), Cys(Bzl), Glu(OBu$^t$), Asp(OBu$^t$), Glu(NH-Bu$^t$), Glu(NH-Et), Lys(Z), Lys(Boc), Orn(Boc), Tyr(Bu$^t$), Tyr(Me), Phe(Cl), Tyr(Cl), tryptophan, and tryptophan substituted by alkyl, halogen, or methoxy, or is an amide, alkyl amide, or alkyl ester having 1-6 carbon atoms of such an amino acid, or is an aralkyl ester having 7-10 carbon atoms of such an amino acid.

10. A peptide as in claim 1 wherein Q is L-Glu.

11. A peptide as in claim 1 wherein Q is D-Glu, D-Asp, or D-Aad.

* * * * *